(12) United States Patent
Ladisch et al.

(10) Patent No.: US 9,359,619 B2
(45) Date of Patent: Jun. 7, 2016

(54) BIOMASS LIQUEFACTION PROCESSES, AND USES OF SAME

(71) Applicant: Purdue Research Foundation, West Lafayette, IN (US)

(72) Inventors: Michael R. Ladisch, West Lafayette, IN (US); Nathan Mosier, West Lafayette, IN (US); Youngmi Kim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/754,352

(22) Filed: Jan. 30, 2013

(65) Prior Publication Data

US 2013/0330788 A1    Dec. 12, 2013

Related U.S. Application Data

(63) Continuation of application No. PCT/US2011/045958, filed on Jul. 29, 2011.

(60) Provisional application No. 61/369,474, filed on Jul. 30, 2010.

(51) Int. Cl.
| | |
|---|---|
| *C12P 7/10* | (2006.01) |
| *C12N 1/22* | (2006.01) |
| *C12P 19/02* | (2006.01) |
| *C12P 19/14* | (2006.01) |
| *C12P 17/04* | (2006.01) |

(52) U.S. Cl.
CPC ... *C12P 7/10* (2013.01); *C12N 1/22* (2013.01); *C12P 17/04* (2013.01); *C12P 19/02* (2013.01); *C12P 19/14* (2013.01); *C12P 2201/00* (2013.01); *Y02E 50/16* (2013.01)

(58) Field of Classification Search
USPC .................................................. 435/126, 165
See application file for complete search history.

(56) References Cited

U.S. PATENT DOCUMENTS

| 7,754,457 B2* | 7/2010 | Foody et al. .................. 435/165 |
| 2004/0231661 A1* | 11/2004 | Griffin et al. ..................... 127/1 |
| 2007/0100162 A1* | 5/2007 | Petrus et al. .................. 562/515 |
| 2010/0086981 A1* | 4/2010 | Latouf et al. .................. 435/139 |
| 2011/0129889 A1* | 6/2011 | Inamdar et al. ............... 435/165 |
| 2011/0250637 A1* | 10/2011 | Kurihara et al. ................ 435/41 |

OTHER PUBLICATIONS

Liu, Shije et al. Membrane Filtration: Concentration and Purification of Hydrolyzates from Biomass. Journal of Biobased Materials and Bioenergy. vol. 2. 2008. pp. 121-134.*
Mosier, Nathan et al. Characterization of Dicarboxylic Acids for Cellulose Hydrolysis. Biotechnology Prog. vol. 17. 2001. pp. 474-480.*
Jorgensen et al., "Liquefaction of Lignocellulose at High-Solids Concentrations", Biotechnology and Bioengineering, vol. 96, No. 5, Apr. 1, 20007 pp. 862-870.
Koostra et al., "Differential effects of mineral and organic acids on the kinetics of arabinose degradation under lignocellulose pretreatment conditions", Biochemical Engineering Journal, 43 (2009) 92-97.
Koostra et al., "Optimization of the dilute maleic acid pretreatment of wheat straw", Biotechnology for Biofuels, 2009, 2:31, 14 pgs.
Kootstra et al., "Comparison of dilute mineral and organic acid pretreatment for enzymatic hydrolysis of wheat straw", Biochemical Engineering Journal 46 (2009) 126-131.
Kumar et al., "Methods for Pretreatment of Lignocelulosic Biomass for Efficient Hydrolysis and Biofuel Production", Ind. Eng. Chem. Res., Mar. 26, 2009, pp. A-O.
Ladisch et al., "Cellulose to Sugars: New Path Gives Quantitative Yield", Science vol. 201, pp. 743-745, Aug. 25, 1978.
Lu et al., "Biomimetric Catalysis for Hemicellulose Hydrolysis in Corn Stover", Biotechnol. Prog. 2007, 23, 116-123.
Lu et al., "Kinetic Modeling Analysis of Maleic Acid-Catalyzed Hemicellulose Hydrolysis in Corn Stover", Biotechnology and Bioengineering, vol. 101, No. 6, Dec. 15, 2008.
Mosier et al., "Rapid Chromatography for Evaluating Adsorption Characteristics of Cellulas Binding Domain Mimetics", InterScience, 86(7) (2004) pp. 756-764.
Mosier et al., Characterization of dicarboxylic acids for cellulose hydrolysis, Biotechnology Progress, vol. 17, No. 3 (2001) pp. 474-480.
Schell, et al., "Dilute-Sulfuric Acid Pretreatment of Corn Stover in Pilot-Scale Reactor", Applied Biochemistry and Biotechnology, vol. 105, No. 1-3 Spring 2003, pp. 69-85.
Tsao et al., "Production of Multifunctional Organic Acids from Renewable Resources", Advances in Biochemical Engineering/Biotechnology, 1099, vol. 65 pp. 243-280.

* cited by examiner

Primary Examiner — Kagnew H Gebreyesus
Assistant Examiner — Nghi Nguyen
(74) Attorney, Agent, or Firm — Woodard, Emhardt, Moriarty, McNett & Henry LLP

(57) ABSTRACT

Described are processes for the liquefaction of lignocellulosic biomass under the digestive action of dicarboxylic acid(s). Such digests can exhibit enhanced flowability, reduced volume, and significant biomass conversion to dissolved components, and can in some embodiments be further liquefied by contact with an enzyme. Products resultant of these steps can be used for their sugar content to manufacture biofuels or other products.

33 Claims, 20 Drawing Sheets

BIOMASS LIQUEFACTION PROCESSES, AND USES OF SAME

This application is a continuation of International Application Serial No. PCT/2011/045973, filed Jul. 29, 2011, which claims the benefit of U.S. Provisional Application Ser. No. 61/369,474 filed Jul. 30, 2010, each of which is hereby incorporated by reference in its entirety.

BACKGROUND

The present invention relates generally to the utilization of lignocellulosic biomass, and in certain embodiments to processes useful for liquefaction of lignocellulosic biomass for utilization of sugars derived therefrom in fermentation or other processes.

As further background, increasing emphasis has been placed in recent years upon finding ways to utilize lignocellulosic biomass to make useful products, such as fuel products. In one field of interest, fuel ethanol has been produced by fermentation of biomass feedstocks derived from plants. Currently, fuel ethanol is commercially produced from feedstocks of cornstarch, sugar cane and sugar beets. These materials, however, find significant competing uses in the food industry, and their expanded use to make fuel ethanol is met with increased prices and disruption of other industries. Alternative fermentation feedstocks and viable technologies for their utilization are thus highly sought after.

Lignocellulosic biomass feedstocks are available in large quantities and are relatively inexpensive. Such feedstocks are available in the form of agricultural wastes such as corn stover, corn fiber, wheat straw, barley straw, oat straw, oat hulls, canola straw, soybean stover, grasses such as switch grass, miscanthus, cord grass, and reed canary grass, forestry wastes such as wood, e.g. aspen wood and sawdust, and sugar processing residues such as bagasse and beet pulp. Cellulose from these feedstocks is converted to sugars, which are then fermented to produce the ethanol.

A difficulty in using lignocellulosic feedstocks is that the useful sugar content of the biomass is largely caught up in natural polymers such as cellulose and hemicellulose, and conditions or agents must be used to convert those polymeric substances to simple sugars. For this reason, research has focused upon methods for processing lignocellulosic biomass to create process feeds containing simple sugars. Some such research has been directed to pretreating lignocellulosic biomass to enhance the susceptibility of the cellulose to conversion to sugars. Such pretreatment processes are designed to break the lignin seal protecting the cellulose and to disrupt the crystalline structure of the cellulose. A variety of pretreatment methodologies have been explored for this purpose; including physical processes such as size reduction, steam explosion, liquid hot water, irradiation, cryomilling, and freeze explosion; and chemical processes such as acid hydrolysis, buffered solvent pumping, alkali or alkali/$H_2O_2$ delignification, solvents, ammonia; and microbial or enzymatic methods.

Despite previous efforts relating to processing lignocellulosic biomass feedstocks and their ultimate use in the production of ethanol, needs remain for improved and alternative biomass utilization processes, including in the production of ethanol or other useful substances from fermentation. In certain of its aspects, the present invention is addressed to these needs.

SUMMARY

Certain aspects of the present invention relate to processes for treating lignocellulosic biomass to achieve substantial liquefaction of the biomass, desirably at least predominantly under the hydrolytic action of one or more dicarboxylic acids, such as maleic acid. In some forms, such processes involve treating wood or other lignocellulosic biomass with one or more dicarboxylic acids, followed by treatment with a cellulolytic enzyme such as a cellulase. Treatment with the dicarboxylic acid(s) has been discovered to rapidly and effectively liquefy substantial percentages of the biomass dry matter while affording high yields in the conversion of hemicellulose in the biomass to monomeric xylose, significantly reducing the volume of the biomass while also improving flowability, and avoiding the excessive formation of degradation products which are inhibitory of fermentive microorganisms such as yeast and bacteria. Such dicarboxylic acid(s) treatments thus, in some embodiments, serve as effective precursor digestions to subsequent cellulolytic enzyme digestion of remaining undissolved solids, even when the latter is conducted in the presence of at least some amount of the fluidized material from the precursor digest composition, and potentially all of it. Accordingly, in one embodiment of the invention, provided is a method for the liquefaction of solid lignocellulosic biomass that includes contacting the biomass with at least one dicarboxylic acid for a period of time and under conditions effective to form an acidic mixture containing liquefied lignocellulosic biomass components and unliquefied lignocellulosic biomass components. The acidic mixture is neutralized to form a neutralized mixture containing the liquefied lignocellulosic biomass components and unliquefied lignocellulosic biomass components. A fluid portion of such a neutralized mixture can contain dicarboxylate anions residual of the dicarboxylic acid(s) used, glucose, xylose, and sugar degradation products such as furfural and/or 5-hydroxymethyl furfural. The neutralized mixture is contacted with a cellulase enzyme for a period of time and under conditions effective to liquefy at least a portion of the unliquefied lignocellulosic biomass. Such overall, multi-step digestion processes can be conducted so as to result in monomeric xylose and glucose yields each readily in excess of 70% based on the initial hemicellulose and cellulose contents, respectively, of the biomass. The dicarboxylic acid(s) digestion and/or its combination with the enzymatic digestion can also be used to effectively process highly concentrated lignocellulosic biomass mixtures, for example exceeding 15% by weight of biomass dry matter.

In another embodiment, the invention provides a method for manufacturing ethanol. The method includes contacting lignocellulosic biomass with a dicarboxylic acid(s) for a period of time and under conditions effective to form an acidic mixture containing liquefied lignocellulosic biomass components including glucose and xylose, and unliquefied lignocellulosic biomass components. The acidic mixture is neutralized as needed to form a neutralized mixture containing the liquefied lignocellulosic biomass components including glucose and xylose, and unliquefied lignocellulosic biomass components. The neutralized mixture is contacted with a cellulase enzyme for a period of time and under conditions effective to liquefy at least a portion of the unliquefied lignocellulosic biomass and form an enzymatically-hydrolyzed mixture including glucose and xylose in addition to that formed in the dicarboxylic acid(s) digestion. A liquid medium containing the formed glucose and xylose fermented to produce ethanol. In some embodiments, at least one clear liquid medium containing amounts of the glucose and xylose is isolated from the digest material and fermented to form ethanol. In other embodiments, the cellulase enzyme digestion is conducted simultaneously with a fermentation of at least amounts of the formed glucose in a simultaneous saccharification and fermentation (SSF) process.

In still another embodiment, the invention provides a method for treating lignocellulosic biomass, comprising contacting a mixture containing a dicarboxylate anions, liquefied lignocellulosic biomass components including xylose and glucose, and unliquefied lignocellulosic biomass components, with a cellulase enzyme for a period of time and under conditions effective to hydrolyze at least a portion of the unliquefied lignocellulosic biomass components. In certain forms, the mixture also includes sugar degradation products such as furfural and/or 5-hydroxyfurfuryl, and potentially also phenolic compounds released or formed from the digestion of the biomass.

In still another embodiment, the invention provides a method for liquefaction of wood biomass that includes forming a mixture including an aqueous solution of a dicarboxylic acid and solid, particulate wood biomass, and incubating the mixture for a period of time and under conditions effective to cause hydrolysis of the wood biomass substantially by the dicarboxylic acid to form a flowable composition. The dicarboxylic acid can be the sole or at least predominant (on a molar basis) protic organic material in the solution, and thus in certain forms the aqueous solution can be free of added, hydroxyl-containing organic solvents such as alcohols. In this fashion, the dicarboxylic acid(s) can be the substantial source of hydrolytic action on the wood biomass, avoiding or at least minimizing the need for other organic reagents which could add to the material cost of the operation and potentially also serve as, or lead to the formation of, inhibitors to later operations imparted upon the wood digest, for example enzymatic hydrolysis and/or fermentation steps. Such wood liquefaction methods can be conducted at relatively high solids concentration, for example at least 15% by weight biomass dry matter in the mixture.

Additional embodiments as well as features and advantages of the invention will be apparent to persons of ordinary skill in the art from the descriptions herein.

DETAILED DESCRIPTION

Figure 1:
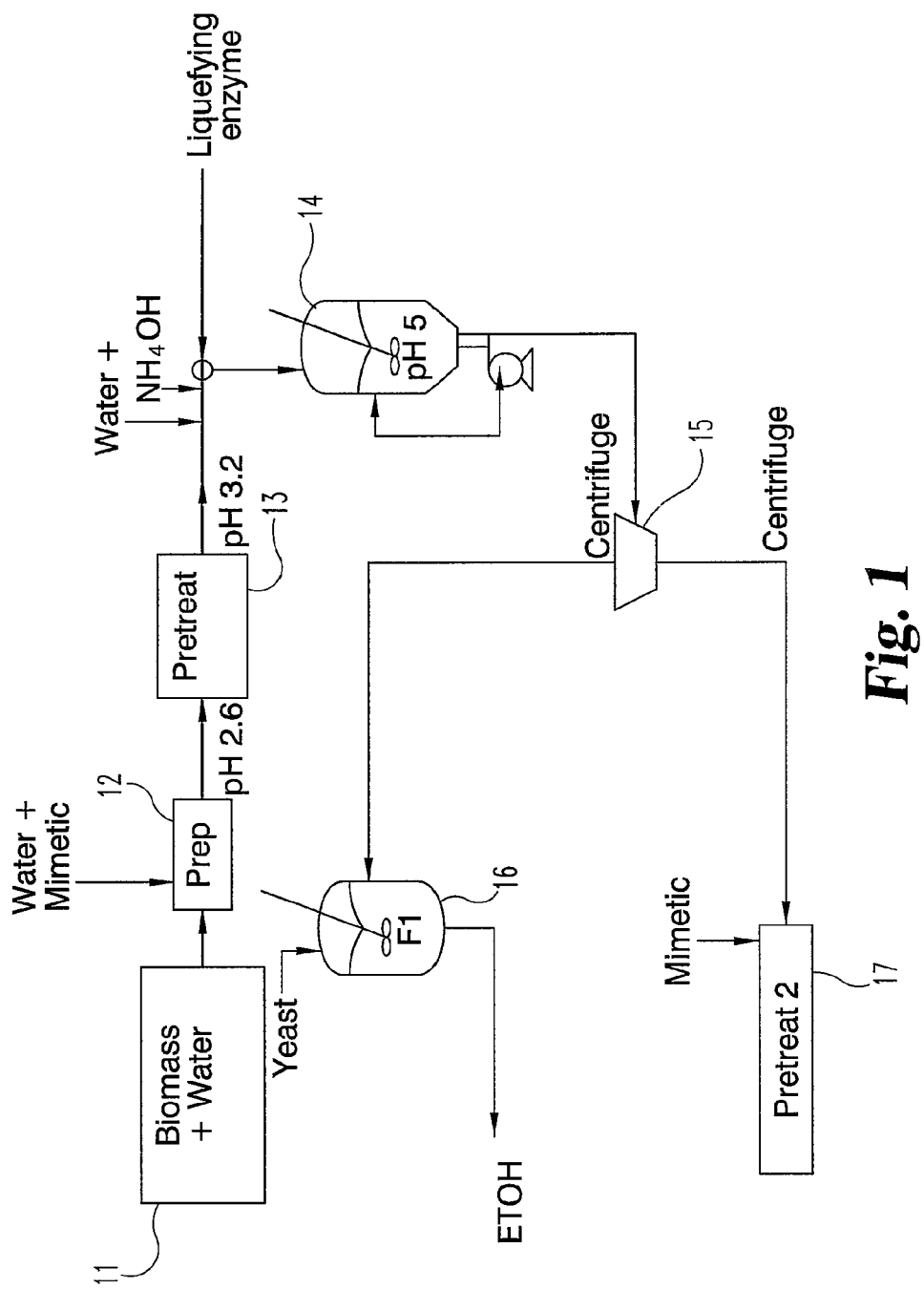
FIG. 1 is a schematic diagram of processing steps in one embodiment of a bioethanol production process of the invention.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated embodiments, and such further applications of the principles of the invention as described herein being contemplated as would normally occur to one skilled in the art to which the invention relates.

As disclosed above, certain aspects of the present invention relate to methods for processing lignocellulosic biomass. As used herein, the term "lignocellulosic biomass", is meant to refer to any type of biomass comprising lignin and cellulose such as, but not limited to, non-woody plant biomass, agricultural wastes and forestry residues and sugar-processing residues. For example, the lignocellulosic feedstock can include, but is not limited to, grasses, such as switch grass, cord grass, rye grass, miscanthus, mixed prairie grasses, or a combination thereof; sugar-processing residues such as, but not limited to, sugar cane bagasse and sugar beet pulp; agricultural wastes such as, but not limited to, soybean stover, corn fiber from grain processing, corn stover, oat straw, rice straw, rice hulls, barley straw, corn cobs, wheat straw, canola straw, oat hulls, and corn fiber; and forestry wastes, such as wood, including but not limited to, recycled wood pulp fiber, sawdust, hardwood, softwood, or any combination thereof. Further, the lignocellulosic biomass may comprise lignocellulosic waste or forestry waste materials such as, but not limited to, paper sludge, newsprint, cardboard and the like. Lignocellulosic biomass may comprise one species of fiber or, alternatively, a lignocellulosic biomass feedstock may comprise a mixture of fibers that originate from different lignocellulosic materials.

Typically, the lignocellulosic material will comprise cellulose in an amount greater than about 2%, 5% or 10% and preferably greater than about 20% (w/w) to produce a significant amount of glucose. The lignocellulosic material can be of higher cellulose content, for example at least about 30% (w/w), 35% (w/w), 40% (w/w) or more. Therefore, the lignocellulosic material may comprise from about 2% to about 90% (w/w), or from about 20% to about 80% (w/w) cellulose, or from 25% to about 70% (w/w) cellulose, or about 35% to about 70% (w/w) cellulose, or more, or any amount therebetween.

Prior to processing with chemical or biological agents, the lignocellulosic biomass can be mechanically processed to increase its surface area. Such mechanical processing may include, for example, reducing the biomass to a particulate by grinding, milling, agitation, shredding, or other types of mechanical action. The particulate biomass feedstock can have a particle size distribution providing an average, maximum particle dimension of at least about 1 mm in certain embodiments, and in typical embodiments at least about 3 mm. In some forms, the average, maximum particle dimension of the particulate biomass feedstock can be within the range of about 1 mm to about 20 mm, more particularly about 3 mm to about 20 mm. When wood biomass is utilized, the wood particles can be provided as a product known as "pin chips", in which elongate wood particles constitute the particulate, and the average, maximum lengths of the wood particles can provide the average, maximum dimensions disclosed above, or even greater dimensions. In some embodiments, large wood pin chip feedstock will be used, for example having average maximum lengths in the range of about 2 to 4 cm and potentially also an average width of about 0.2 to 1 cm. Such pin chip wood products, and other particulate wood products, can be free from bark, or can contain bark.

Besides mechanical processing as described above, the lignocellulosic feedstock may also be subjected to other processes to physically disrupt its native structure. Illustratively, the biomass can be steam exploded or treated under pressure with hot water prior to use in the chemical or biological processes described herein.

The lignocellulosic biomaterial feedstock will usually contain some level of moisture prior to its combination with aqueous or other mediums as described herein. Moisture contents in the range of about 20% to about 70% by weight will be typical, depending upon the type of biomass, source, prior processing, and other factors. For wood biomass, the initial moisture content will typically be in the range of about 40% to 50% by weight.

It has been discovered that the hydrolytic action of dicarboxylic acids can be used to rapidly achieve substantial liquefaction of particulate lignocellulosic biomass in a fashion that advantageously eases flow transport of the biomass and reduces downstream material volume, while also avoiding excessive formation of undesired degradation products. The dicarboxylic acid(s) acts like an enzyme mimic in the hydrolysis of components of the biomass, thus avoiding or significantly reducing the need to use enzymes to hydrolyze these materials in achieving liquefaction. A variety of dicarboxylic acids may be used alone or in combination in the liquefaction of the lignocellulosic biomass. Maleic acid (e.g. provided to the medium as maleic acid or maleic anhydride) and/or succinic acid (e.g. provided to the medium as succinic acid or succinic anhydride) and/or oxalic acid may be used in certain embodiments of the invention. Maleic acid is preferred from work to date.

To achieve liquefaction of at least a portion of the biomass, a mixture of the biomass with a liquid medium containing the dicarboxylic acid(s) can be prepared. The liquid medium is desirably aqueous, preferably at least about 60% by weight aqueous, more preferably at least about 80% by weight aqueous, and most preferably about 90% to about 99.9% by weight, or more, aqueous. The use of highly aqueous mediums avoids or minimizes the need to use other solvent materials, such as organic solvents, for the liquefaction. Such organic solvents would typically add significantly more material cost than water. In particularly beneficial embodiments, the pretreatment medium will be constituted 97% to 100% by weight of water and dicarboxylic acid(s).

In one mode, the dicarboxylic acid, or its corresponding acid anhydride, can be added to water to form a liquid dicarboxylic acid medium. The resulting aqueous solution of the dicarboxylic acid can then be combined with the biomass to form the mixture. In other modes, the biomass can be combined with added water, followed by addition of the dicarboxylic acid(s) or their corresponding anhydrides. These and other methods of preparing the biomass/medium mixture are contemplated as within the invention.

The dicarboxylic acid is desirably present at a relatively low concentration in the overall mixture, for example in the range of about 0.1 to about 5% by weight relative to the weight of biomass solids dry matter, with this value more typically being in the range of about 0.1% to 2% by weight, and preferably in the range of about 0.1 to about 1% by weight. In certain particularly preferred processes, the dicarboxylic acid is present in the overall mixture at a concentration of about 0.2% to about 0.5% by weight relative to the biomass solids dry matter. Because it has been discovered that the dicarboxylic acid(s) can, through its own hydrolytic action, substantially liquefy the biomass, the use of any other organic or inorganic reagents in the treatment solution can be avoided altogether or at least minimized. In certain embodiments, on a molar basis, the dicarboxylic acid(s) is the predominant (over 50%) protic organic substance in the solution of the starting biomass mixture, or constitutes at least 80% or at least 90% of the total protic organic substance(s) in the solution of the starting biomass mixture. The dicarboxylic acid(s) can be essentially the only protic organic substance(s) in or added to the starting biomass mixture, or essentially the only protic substance of any kind in or added to the starting biomass mixture (other than water, when an aqueous solution is used); it will be understood in these embodiments that trace amounts of organic or other protic substances may nonetheless be present as impurities (e.g. less than about 0.3% by weight). The use of the dicarboxylic acid(s) as the substantial or only hydrolytic reagent can avoid the use of other chemical reagents which add to material costs and potentially serve as or lead to the formation of inhibitors of later processing steps such as enzymatic hydrolysis and/or fermentation. It is contemplated that in certain embodiments, however, that ethanol may be included along with the dicarboxylic acid(s) in the starting biomass mixture, for example in certain processes at a level of about 0.5% to about 20% by weight relative to the weight of the dry biomass matter. When the dicarboxylic(s) acid digestion is a part of a process for producing ethanol such as described herein, a portion of the product ethanol can be diverted to the starting biomass mixture for these purposes. The presence of ethanol in such processes may for example be useful to result in a greater conversion of the biomass to dissolved substances and/or to better condition undissolved matter for subsequent treatment with a cellulase enzyme.

The dicarboxylic acid-containing liquid medium can be combined with the biomass solids in any suitable ratio to facilitate achieving at least partial liquefaction of the solids. In some forms, the biomass and liquid medium will be combined in amounts to provide an overall liquids/solids mixture constituted at least about 3% by weight of the biomass solids on a dry weight basis, and typically in the range of about 3% to about 40% by weight. In certain preferred forms, the biomass solids will constitute at least about 10% by weight of the mixture on a dry weight basis, for example about 10% to about 40%, or at least about 15% by weight of the mixture on a dry weight basis, for example about 15% to about 35%.

Aqueous dicarboxylic acid(s) solutions to be combined with the biomass to form mixtures as described above can have any suitable concentration of the dicarboxylic acid(s). In certain processes, a starting aqueous dicarboxylic acid solution will include maleic acid and/or other dicarboxylic acid(s) at a total concentration in the range of about 10 mM to about 100 mM of the dicarboxylic acid(s).

The biomass can be incubated in contact with the dicarboxylic acid-containing liquid medium at any temperature effective to provide at least partial liquefaction of the biomass. Elevated temperatures can be employed, for example a temperature greater than about 100° C., and typically in the range of about 100° C. to about 210° C. In certain processes, the biomass/liquid preparation will be subjected to heating within a temperature range of about 170° C. to about 210° C. In certain other processes, a relatively low temperature digestion will be conducted, with heating controlled within a temperature range of about 120° C. to about 155° C. Surprisingly, it has been found that in such low temperature digestions, even when using relatively long incubation times, such as greater than about 1 hour, e.g. 1 to 24 hours, the formation of sugar degradation products such as furfural and/or 5-hydroxymethylfurfural is very low, and the selectivity for xylose and glucose monomers is enhanced. The dicarboxylic acid(s) thus closely mimic the selective action of an enzyme which can be capitalized upon in low temperature processing, which is contrasted to the behavior of conventional inorganic acids such as sulfuric acid, which exhibit lower selectivity for the sugars under longer incubation periods at relatively low temperatures. Heating at elevated temperatures such as those described herein can be conducted at elevated pressure, for example a pressure sufficient to maintain the starting liquid pretreatment medium in its liquid state, e.g. in the case of aqueous pretreatments the pressure can be maintained above the saturation vapor pressure of water during the heating.

During the incubation, the biomass-containing mixture can be stirred or otherwise mixed to improve digestion of the biomass. However, it has been discovered that the dicarboxylic acid(s) can effectively liquefy the biomass even in the absence of mixing. Thus, in certain forms, incubations in the presence of the dicarboxylic acid(s) are performed partially or completely in the absence of mechanical mixing. This simplifies equipment needs for the operation, saves wear and tear, and avoids energy usage that would otherwise be needed to move the biomass, particularly in its initial unliquefied state. Accordingly, in variants of the processes described herein, at least an initial unmixed dicarboxylic acid(s) incubation period is conducted to partially liquefy the biomass, for example a period of at least about 1 minute. Subsequent to the initial unmixed period, alternate forms can be completed with mixing, or without mixing, during the heated incubation period.

The incubation of the biomass in contact with the dicarboxylic acid-containing medium can be for any suitable period of time for at least partial liquefaction. In certain embodiments, the biomass/liquid mixture will be heated, e.g. within a temperature range disclosed above, for about 1 minute to about 60 minutes, more typically from about 3 minutes to about 30 minutes. Certain preferred embodiments will involve such heating of the biomass/liquid mixture for a period of about 3 minutes to about 15 minutes. As noted above, in other embodiments, longer incubation periods with the dicarboxylic acid(s), such as 1 to 24 hours, will be utilized under temperature conditions sufficiently low to achieve high selectivity for xylose formation, for example to provide (xylose+soluble xylose oligomer):(furfural) molar ratios in the digested medium above about 10, or above about 20. Such low temperature processes are conducted at a temperature in the range of about 120° C. to about 155° C. in certain embodiments.

After the heated dicarboxylic acid(s) digestion, thermal energy from the digested material can be recovered and used to heat new, incoming materials to the process such as dicarboxylic acid(s) solution or biomass. U.S. Patent Application Ser. No. 61/369,445 entitled "LIQUEFACTION BIOMASS PROCESSING WITH HEAT RECOVERY", filed on Jul. 30, 2010, which is incorporated herein by reference, describes heat recovery operations that can be used in the processes described herein.

Treatment of lignocellulosic biomass feedstock at appropriate concentrations, times and temperatures using dicarboxylic acid(s) may be used to achieve above about 70% hydrolysis of hemicellulose in the biomass to monomeric xylose, preferably above about 80%, and more preferably above about 90%. These treatments can also result in a total monomeric xylose content in the digest composition of at least about 10 g/L, more preferably at least about 15 g/L, and typically in the range of about 15 g/L to about 30 g/L. In some forms of practice, a liquefied fraction of biomass from a dicarboxylic acid(s) digestion, for example containing solubilized components as described herein, can be contacted with additional starting lignocellulosic biomass alone or with additional fresh dicarboxylic acid(s) solution to result in the hydrolysis of hemicellulose in the additional starting biomass and potentially a resultant liquefied fraction having an increased xylose monomer content as compared to the liquefied fraction from the initial digestion. The xylose in the digested medium, and potentially also smaller amounts of glucose therein, can then be fermented to ethanol as described herein. Such digestion processes can be conducted in batch or continuous modes, for example in some embodiments using countercurrent processing techniques for contact of new amounts of the biomass with the previously liquefied fraction alone or combined with fresh maleic acid solution, and/or wash solution if needed or desired. The unliquefied large particulate matter resultant of such processes, substantially depleted of hemicellulose but enriched in cellulose, can be processed with cellulase enzymes and fermented to ethanol as described herein, or can be dried and put to other use, such as for its fuel value by burning the material to generate heat that is at least in part fed to the dicarboxylic acid(s) digestion process. In the latter case an ethanol biofuel operation based completely or primarily on xylose fermentation can be provided.

At the completion of the liquefaction treatment with the dicarboxylic acid(s), the resulting composition will typically be characterized as a mixed, acidic liquid/solid composition having significantly more flowable liquid material than the initial mixture, with the flowable liquid material including the dicarboxylic acid(s), dissolved xylose and glucose monomers derived from digestion of the biomass, and suspended finely divided biomass particles that flow freely with the liquid material. The flowable liquid material can also include minor amounts of furfural from the degradation of xylose and 5-hydroxymethylfurfural (HMF) from the degradation of glucose, and/or phenolic compounds liberated or formed from the biomass. The dicarboxylic acid(s) liquefaction will desirably be controlled to keep the formed furfural to less than about 8 g/L, more preferably less than about 5 g/L, and/or the formed HMF to less than about 5 g/L, more preferably less than about 2 g/L. The overall treated composition will typically also include some larger, partially-digested particles of the biomass which are enriched in lignin and glucan and which do not suspend and flow freely with the liquid portion of the composition, such that they can readily be separated even without filtration, by pouring or otherwise draining off the liquid portion of the treated overall composition, e.g. by centrifugation, to leave behind the larger particle material.

The dicarboxylic acid(s) digest process can be conducted to cause a substantial increase in the bulk density of the biomass solids dry matter. For example, the digestion can be conducted to as to increase the bulk density of the biomass dry matter by at least about 15%, more preferably at least about 30%. As will be understood, these increases in solids bulk density also provide a reduction in the volume of the wet mixture during the processing. In addition or alternatively, a substantial percentage of the original biomass dry matter can be converted to solubilized components during the dicarboxylic acid(s) digestion. For instance, in certain embodiments at least about 20% of the original biomass dry matter is converted to solubilized solids by the dicarboxylic acid(s) digestion, more preferably at least about 30%, and typically in the range of 20% to about 60%.

In one mode of use, at least a portion of the dicarboxylic-acid-treated composition including the partially-digested particles and some of the flowable liquid material, and potentially the entirety of the dicarboxylic-acid-treated composition, is subjected to enzymatic hydrolysis to further liquefy the composition. Where an enzyme is used that is inactive or insufficiently active at the acidic pH of the dicarboxylic acid-treated composition, the pH of the composition can be increased (i.e. the composition can be neutralized) to a level suitable for the enzyme, for instance a pH in the range of about 4 to 7 at which the enzyme is active. Any suitable basic substance can be used for such neutralization, such as an alkali or alkaline earth metal hydroxide such as sodium hydroxide and/or calcium hydroxide, and/or ammonium hydroxide. Such a neutralized composition will typically thereby contain a corresponding salt(s) of the dicarboxylic acid used for the hydrolytic liquefaction of the original biomass feedstock. Surprisingly, it has been discovered that the enzymatic hydrolysis process can be conducted to good effect on the dicarboxylic acid-treated biomass composition without prior removal of potentially inhibitory components such as furfural, HMF, phenols and/or other compounds from the composition by washing or other means.

The enzymatic hydrolysis can be conducted with a cellulase enzyme. In this regard, a cellulase enzyme is an enzyme that catalyzes the hydrolysis of cellulose to products such as glucose, cellobiose, and/or other cellooligosaccharides. Cellulase enzymes may be provided as a multienzyme mixture comprising exo-cellobiohydrolases (CBH), endoglucanases (FG) and beta-glucosidases (betaG) that can be produced by a number of plants and microorganisms. The process of the present invention can be carried out with any type of cellulase enzymes, regardless of their source; however, microbial cellulases provide preferred embodiments. Cellulase enzymes can, for example, be obtained from fungi of the genera *Aspergillus, Humicola*, and *Trichoderma*, and from the bacteria of the genera *Bacillus* and *Thermobifida*.

The treatment of the biomass with the dicarboxylic acid(s) has been found to condition the remaining, partially-digested particulate material in a fashion that renders it more susceptible to the action of cellulase enzymes which digest glucan present to form glucose and soluble gluco-oligomers. While any suitable enzyme loading can be used to further treat the biomass composition or its undigested components, for example a loading in the range of up to about 20 FPU (Filter Paper Units) (Adney, W. and Baker, J. "Measurement of Cellulase Activities," Laboratory Analytical Procedure (LAP) 006, National Renewable Energy Laboratory, 1996) of enzyme per gram of glucan in the original biomass feedstock (prior to the dicarboxylic acid treatment), it has been discovered that low enzyme levels can be effectively used and thus cellulase enzyme loadings less than about 3 FPU per gram of original glucan are desirably used, preferably less than 2 FPU per gram of original glucan, and in certain embodiments about 1.5 FPU or less per gram of original glucan, wherein in each of these cases a minimum of about 0.1 FPU per gram of original glucan can optionally be employed. In certain preferred embodiments, a low cellulase enzyme loading in the range of about 0.5 FPU to about 1.5 FPU per gram of original glucan is used. These low loadings provide significant material cost savings due to the expense of the relevant enzymes. In terms of milligrams of cellulase enzyme per gram dry matter of original biomass, the cellulase enzyme can be used again at any suitable level, for example at a loading in the range of up to about 10 mg of enzyme per grain of original biomass feedstock. Again, however, low enzyme levels can be effectively used and thus such cellulase enzyme loadings less than about 3 mg of enzyme per gram of original biomass are desirably used, preferably less than 2 mg enzyme per gram of original biomass, and more preferably less than about 1.5 mg enzyme per gram of original biomass, wherein in each of these cases a minimum of about 0.1 mg enzyme per gram of original biomass can optionally be employed. In certain preferred embodiments a low cellulase enzyme loading in the range of about 0.3 mg to about 1 mg enzyme per gram of original biomass dry matter is used.

The enzyme hydrolysis process can be conducted for a suitable duration to achieve significant conversion of cellulose from the biomass to monomeric glucose. Durations may for example be from about 1 hour up to about 72 hours, more typically in the range of about 6 hours to about 36 hours, and in some embodiments about 10 to 30 hours. Such processes can be conducted in any suitable vessel, including for example stirred tank fermentation vessels. Such processes can be conducted so as to achieve conversion of at least about 15% by weight of the original cellulose to monomeric glucose, an in more beneficial processes at least about 50% by weight, for instance in the range of about 50% to about 100% by weight.

It has been discovered that hydrolytic treatment of lignocellulosic biomass sequentially with a dicarboxylic acid(s) and an enzyme(s) as described herein not only provides an effective conversion of the biomass to monomeric sugars including glucose and xylose, but can also yield a liquefied, flowable biomass preparation with beneficial rheological properties for subsequent processing operations. In this regard, it is known that concentrated biomass slurries encountered in prior art processing have been highly viscous, strongly shear-thinning materials, exhibiting high levels of concentration-dependent yield stress (the stress at which a material begins to deform plastically). This imposes power requirements upon pumps, mixers and other processing equipment typically used in biomass conversion, since these devices must have sufficient power to overcome the yield stress of the material to cause its movement. Preferred biomass compositions treated sequentially with dicarboxylic acid and enzymatic hydrolysis herein will exhibit yield stresses of less than about 3000 Pascals, more preferably less than about 1000 Pascals. In the applicants' work, such yield stresses have been determined by extrapolating shear rate versus shear stress using the Bingham model: $\tau=\eta_p\gamma+\tau_y$; where $\tau$=shear stress (Pa); $\gamma$=shear rate (1/s); $\tau_y$=Bingham yield stress (Pa); and $\eta_p$=plastic viscosity (Pa·s). Additional details are found in Example 6 below, and can also be found in Howard A. Barnes, *The yield stress—a review—everything flows?*, J. Non-Newtonian Fluid Mech. Vol. 81, 133-178 (1999).

The treated biomass preparation resultant of the initial dicarboxylic acid treatment or resultant of such treatment in combination with an enzymatic hydrolysis can be processed by fermentation or otherwise to yield useful products, including biofuel products. In preferred forms, monomeric sugar(s) at either of these treatment stages can be charged directly or indirectly to a fermentation process for conversion to organic substances, especially ethanol.

In certain embodiments, the biomass feedstock is fed through both the dicarboxylic acid and enzymatic hydrolysis without any fractionation, and thereafter the flowable, liquefied material is separated from the remaining partially-digested biomass solids, for example by centrifugation. The liquefied material, which in some embodiments comprises at least about 3% by weight monomeric pentose sugars (e.g. xylose) and typically about 3% to about 6% by weight is then charged to a fermentation unit for conversion of the xylose and/or other pentose sugars, and potentially also glucose (usually at a lower concentration, e.g. less than about 2% by weight), to ethanol. The fermentation of the sugar(s) to produce ethanol can be conducted with any of a wide variety of fermentive microorganisms such as yeast or bacteria, including genetically modified versions thereof, and using known techniques. The ethanol can then be purified from the fermented medium, for example by distillation. The solids material recovered from the separation can be subjected to further hydrolytic treatment by acid(s) or enzymes to reduce biomass components to provide additional amounts of monomeric sugars such as xylose and/or glucose can be fermented to provide ethanol which can be recovered for example by distillation, all as described above. In a preferred embodiment, the recovered solids are first hydrolyzed with a dicarboxylic acid(s), for example under conditions as described hereinabove, and a clear liquid fraction (essentially free of suspended solids) containing sugars, typically predominant in xylose but also potentially containing other pentoses and glucose, can be separated from the remaining solids and fermented to ethanol. Such fermentations can be conducted as described above. The remaining solids from the second dicarboxylic acid(s) treatment can then be neutralized as appropriate and hydrolyzed with an enzyme to yield glucose, which can be fermented to ethanol. This enzyme hydrolysis can be conducted under conditions as described hereinabove, but in preferred embodiments is conducted using consolidated bioprocessing in which enzyme hydrolysis and fermentation are conducted simultaneously. Such consolidated bioprocessing achieves simultaneous saccharification and fermentation (referred to as "SSF") of the biomass material using yeast or another microorganism(s) that expresses a cellulolytic enzyme(s) as well as converts the glucose (and potentially also xylose) to ethanol, or a yeast or other microorganism(s) that is thermotolerant and can effectively ferment the sugar(s) in the presence of added cellulase enzyme(s).

In this regard, suitable microorganisms for such SSF processing or conventional fermentation processing include for example genetically-modified or non-genetically-modified yeast, including for example *Saccharomyces cerevisiae*. Other yeasts for fermentation may include pentose fermenting yeast, cellulose fermenting yeast, cellulobiohydrase- and/or endoglucanase expressing yeast, *Clostridium thermocellum* or *Thermoanaerobacterium saccharolyticum*, either of which has been genetically modified to ferment glucose, xylose, and/or cellulose to ethanol, thermotolerant strains of yeast such as *Saccharomyces cerevisiae* SERI strain ($D_5A$), *Saccharomyces uvarum*, *Candida* genera *acidothermophilium*, *brassicae*, and *lusitaniae*, *Brettanomyces clausenii* (Y-1414), *Kluyveromyces marianus*, and others. At the conclusion of the consolidated bioprocessing, the fermented medium can be charged to a separator such as a stripper unit to separate the solids (rich in lignin) from a liquid medium containing the ethanol, and the liquid medium can be processed to purify the ethanol such as by distillation.

In additional embodiments, the biomass digest composition resultant of the dicarboxylic acid(s) and enzymatic hydrolysis can be fermented as a whole in a single fermentation, desirably utilizing a microorganism such as a yeast that can convert both xylose and glucose to ethanol, or a combination of microorganisms to accomplish this goal. Such a fermentation may also be an SST process as described above, achieving hydrolysis of glucan to glucose simultaneously with fermentation of the glucose (and potentially also xylose) to ethanol. Still other modes of use of the dicarboxylic acid(s) digest composition or the follow-on enzymatic digest composition to produce ethanol or other useful organic products will be apparent to those of ordinary skill in the art from the descriptions herein.

In still further aspects, at least a portion of the dicarboxylic acid(s) used in treating the biomass can be recovered and recycled to treat additional amounts of biomass, for example as described in U.S. Patent Application Ser. No. 61/251,034 filed Oct. 13, 2009 entitled "PROCESS FOR PREPARING ENRICHED GLUCAN BIOMASS MATERIALS," which is hereby incorporated herein by reference in its entirety. Thus, in ethanol production processes described herein, after ethanol has been recovered from the neutralized fermentation material by, for example distillation, the material remaining is rich in the dicarboxylic acid. The dicarboxylic acid can then be recovered from this material, for example, by distillation. Once the recovery step is complete, the dicarboxylic acid can be recycled to the front of the process to treat additional amounts of lignocellulosic biomass. If desired, the distillation can be carried out under a vacuum in order to minimize formation of salts in the bottoms from the distillation column and also preserve the activity of the dicarboxylic acid. For example, maleic acid has a high boiling point and is stable up to 220° C., and may be recovered and concentrated in the bottoms stream of the fermentation distillation column itself. Further evaporation would then give a concentrated maleic acid stream which would then be recycled to the front end of the process for further treatment of additional lignocellulosic biomass.

For the purpose of promoting a further understanding of certain inventive embodiments, as well as their features and advantages, the following specific Examples are provided. It will be understood that these Examples are illustrative, and not limiting, of the invention.

Example 1

Liquefaction of Wood Biomass with Dicarboxylic Acid

This example demonstrates the liquefaction of cellulose-rich solids of pretreated mixed hardwood solids using an aqueous solution of a dicarboxylic acid (maleic acid). Mixed hardwood was liquid hot water pretreated at 12% w/w dry solids loading at 200° C. for 20 min. The pretreated mixed hardwood was hot-water washed to remove solubles. The pretreated/hot-washed mixed hardwood contained 55% glucan and no measurable xylan, arabinan, and acetyl. Dicarboxylic acid (maleic acid) treatment of the liquid hot water pretreated/washed solids of mixed hardwood was conducted by mixing the substrate with 1% w/w maleic acid at 15% solids loading (w/w, g dry solids per g total) and heating at 210° C. for 20 min under pressure in order to keep the water in a liquid state. Reactions were conducted in 1 in. OD×0.083 in. (2.54 cm×2.1 mm) wall thickness, 316 stainless steel tubing capped at both ends with 1 in. (2.54 cm) Swagelok tube end fittings (Swagelok, Indianapolis, Ind.). Each tube was 4.5 in. (11.4 cm) in length and 45 mL in total volume. The sample volume was kept at 33.7 mL to give approximately 25% of head space for liquid expansion during heating to 200° C. The reactor tube containing the slurry of wood biomass was heated by placing it in a Tecam® SBL-1 fluidized sand bath (Cole-Parmer, Vernon Hills, Ill.) set to 210° C. for 30 min, which included a 10 min heat-up and 20 min reaction time. After pretreatment, each tube was cooled by quenching in water for 10 minutes.

Example 2

Two-Stage Liquefaction and Fermentation

This example demonstrates further liquefaction of dicarboxylic-acid-treated wood biomass can be achieved with a cellulolytic enzyme, and that the resulting treated medium can be fermented to ethanol.

Samples of liquefied slurry prepared as in Example 1 were enzymatically hydrolyzed using 15 FPU Spezyme CP/40 CBU Novozyme 188/g glucan and 200 OSX Multifect Pectinase/g xylan or 1.5 FPU Spezyme CP/4 CBU Novozyme 188/g glucan and 200 OSX Multifect Pectinase/g xylan in the liquefied slurry. Hydrolysis was carried out at 50° C., pH 4.8, with stirring at 250 rpm for 24 hours. The resulting hydrolysate was adjusted to pH 6.0 and continued for fermentation using *Saccharomyces cerevisiae* ATCC 4124. The fermentation was carried out at 28.5° C. for 48 h using the *Saccharomyces cerevisiae* ATCC 4124. 8 mL of seed culture was used to inoculate 100 mL YEPD (YEP plus 2% glucose) in a 300 mL baffled sidearm Erlenmeyer flask. The cultures were incubated in a shaker at 28.5° C. and 200 rpm and grown aerobically overnight, after which a cell optical density (OD) between 450-500 KU was obtained. The yeast cells were harvested by centrifugation (J-21 Beckman) at 5000 rpm for 5 minutes at 4° C. The supernatant was discarded and the cells were transferred into a 300 ml, baffled Erlenmeyer flask containing 100 mL of either synthetic YEP medium (for the furfural/acetic acid effects experiments) or the poplar hydrolysate from enzymatic hydrolysis. The initial cell mass concentration prior to fermentation in each experiment was about 5 g dry weight/L. The flasks were then sealed with Saran wrap to allow fermentation to be carried out under largely anaerobic conditions. The cultures were placed in shaker and incubated at 30° C. and 200 rpm. At regular intervals 1 mL samples of the fermentation mixture was removed for monitoring the fermentation. The fermentation experiments were run in duplicate and demonstrated successful fermentation of the biomass to produce ethanol.

Example 3

Bioethanol Production Process

Described in this example is a multi-stage process for producing ethanol from lignocellulosic biomass. General processing steps are referenced which correspond to discussions in the Detailed Description above. Processing steps referenced in this example can utilize any of the materials and/or conditions referenced in the corresponding discussions above. Thus, where materials or conditions are specified in this example, they can be replaced by materials or conditions for corresponding processing steps discussed in the Detailed Description above, and where materials or conditions are not specified in this example, those described above can be used.

With reference to FIG. 1, a feed input 11 of biomass and water (2000 pounds each) is fed to a preparation tank 12. Water (1000 pounds) having dissolved therein an enzyme mimetic (maleic acid, in the form of maleic anhydride, 20 pounds) is combined with the biomass in a preparation vessel 12. The resulting mixture, having a pH of about 2.6, is heated in a pretreatment unit 13, such as a pressure vessel (which can optionally also serve as the preparation vessel 12). Heat is provided by direct injection of steam into the material, adding 1000 pounds of water to the overall mixture. After a heat-up period (about 5 minutes), the material is held at a temperature of about 200° C.±5° C. for about 10 minutes. The resulting mimetically-hydrolyzed mixture, pH about 3.2, is combined with water (3000 pounds) having dissolved therein sufficient ammonium hydroxide to adjust its pH to about 5 (e.g. about 10 pounds), and the neutralized mixture and cellulase enzyme (about 2.25 pounds) are thereafter incubated in a stirred tank 14 for about 24 hours. After this cellulase hydrolysis step, the resulting hydrolyzed material is transferred to a centrifuge 15. Centrifuge 15 separates the material into a fraction depleted of undissolved solids and a fraction rich in undissolved solids. The depleted fraction contains 19-20% by weight dissolved solids representing about 800 pounds of the original 2000 pounds of biomass input to the process. The depleted fraction, containing monomeric xylose (about 9% w/w) and lesser amounts of glucose, and residual dissolved maleate and ammonium ionic species, is charged to a fermentor 16 and fermented with yeast over about 70 hours to convert the xylose and potentially also the glucose to form ethanol. A fermented medium containing 37-38% ethanol can be obtained from fermentor 16.

Figure 2:
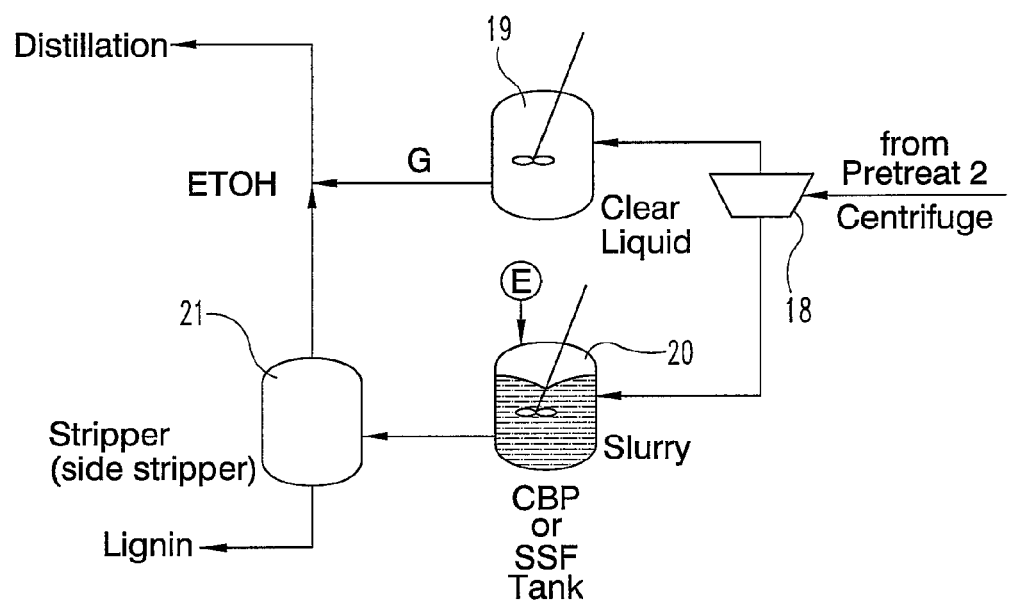
FIG. 2 is a schematic diagram of additional processing steps of the embodiment of FIG. 1.

The undissolved solids-enriched fraction from centrifuge 15 containing water, biomass constituents (representing about 1200 of the original 2000 pounds) and maleate and ammonium ions, is transferred to a second-stage pretreatment unit 17, such as a pressure vessel, along with added maleic acid (added as maleic anhydride, 5 pounds) and heated as described above for unit 13 to hydrolyze biomass components under the action of the maleic acid and form monomeric xylose and a smaller amount of monomeric glucose. Referring now to FIG. 2, the pretreated material from unit 17 is transferred to centrifuge 18 where it is separated into an undissolved solids-depleted fraction (essentially clear liquid) and an undissolved solids-enriched fraction. The clear liquid fraction, rich in xylose and containing smaller amounts of glucose, is charged to fermentor 19 where the xylose (and potentially also glucose) is fermented to ethanol with yeast. The undissolved solids-enriched fraction from centrifuge 18 is transferred to a fermentor 20 along with yeast where it is subjected in a slurry to simultaneous saccharification and fermentation (SSF) in which glucan of the biomass is converted to glucose and the glucose is fermented to ethanol in the same processing unit. The resulting fermented medium is transferred to a side stripper unit 21 to separate the solids (rich in lignin) from the ethanol-containing liquid. The liquid from stripper 21 is combined with the fermented medium from fermentor 16 and the mixture is distilled to yield purified ethanol.

Example 4

Liquefaction of Mixed Hardwood Under Varied Conditions

This example demonstrates substantial liquefaction of mixed hardwood pin chips under various temperature and time conditions using and aqueous solution of maleic acid at a maleic acid concentration of 1% wt/wt relative to the hardwood pin chips (dry weight basis). Samples (50-100 g each) of the mixed hardwood pin chips (average particle length about 0.5-1.0 inch) were soaked in the maleic acid solution overnight at solids loadings of 15% or 35%. The next day, in a sealed reaction vessel, the slurry was preheated to 140° C. for 10 minutes (essentially no reaction occurring) and then moved to a sandbath heated to the target temperature (190, 195, 200, 205, or 210° C.). The samples were then given a heat-up time of 5 minutes and then kept in the sandbath for an additional period of 5, 10, 15, 20 or 30 minutes. Substantial liquefaction was achieved in the runs at 15% solids loading under the conditions tested; for 35% solids loading the observed liquefaction was much lower, although reagent and/or physical processing parameters could be adjusted to improve results at these higher loadings. The 15% solids runs are summarized in Table 1 and the results are discussed in conjunction with corresponding Figures below.

TABLE 1

| Temperature (Celcius) | Reaction Time (min) | Heat up time (min) | Total time (min) | Maleic acid conc (%) wt/wt dry biomass | % Solids Loading |
|---|---|---|---|---|---|
| 190 | 10 | 5 | 15 | 1 | 15% |
| 200 | 5 | 5 | 10 | 1 | 15% |
| 200 | 10 | 5 | 15 | 1 | 15% |
| 205 | 5 | 5 | 10 | 1 | 15% |
| 210 | 5 | 5 | 10 | 1 | 15% |
| 195 | 20 | 5 | 25 | 1 | 15% |
| 200 | 15 | 5 | 20 | 1 | 15% |
| 205 | 10 | 5 | 15 | 1 | 15% |
| 210 | 10 | 5 | 15 | 1 | 15% |
| 200 | 20 | 5 | 25 | 1 | 15% |
| 210 | 30 | 5 | 35 | 1 | 15% |

Figure 3:
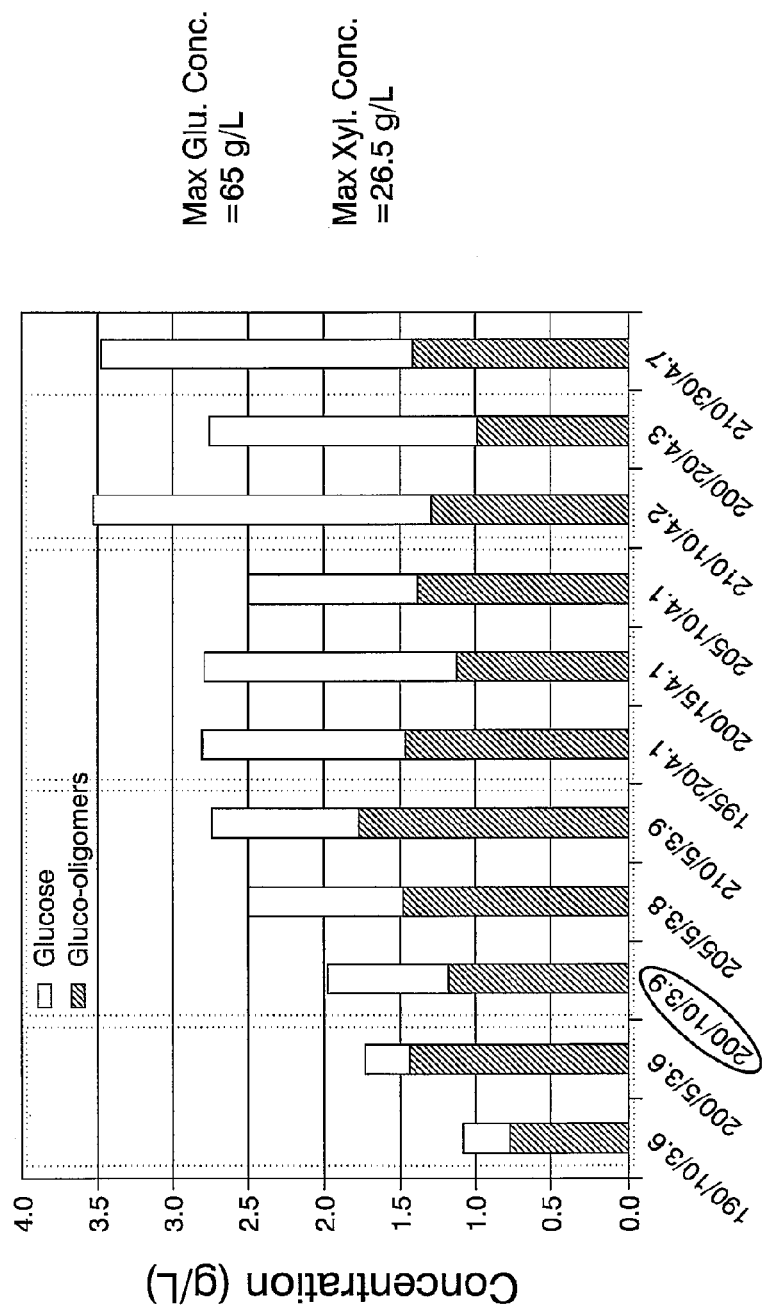
FIG. 3 provides a graph of glucose and gluco-oligomer concentration from treatment of 15% dry solids of mixed hardwood with 1% maleic acid under varied temperature/time conditions, as described further in Example 3.
Figure 4:
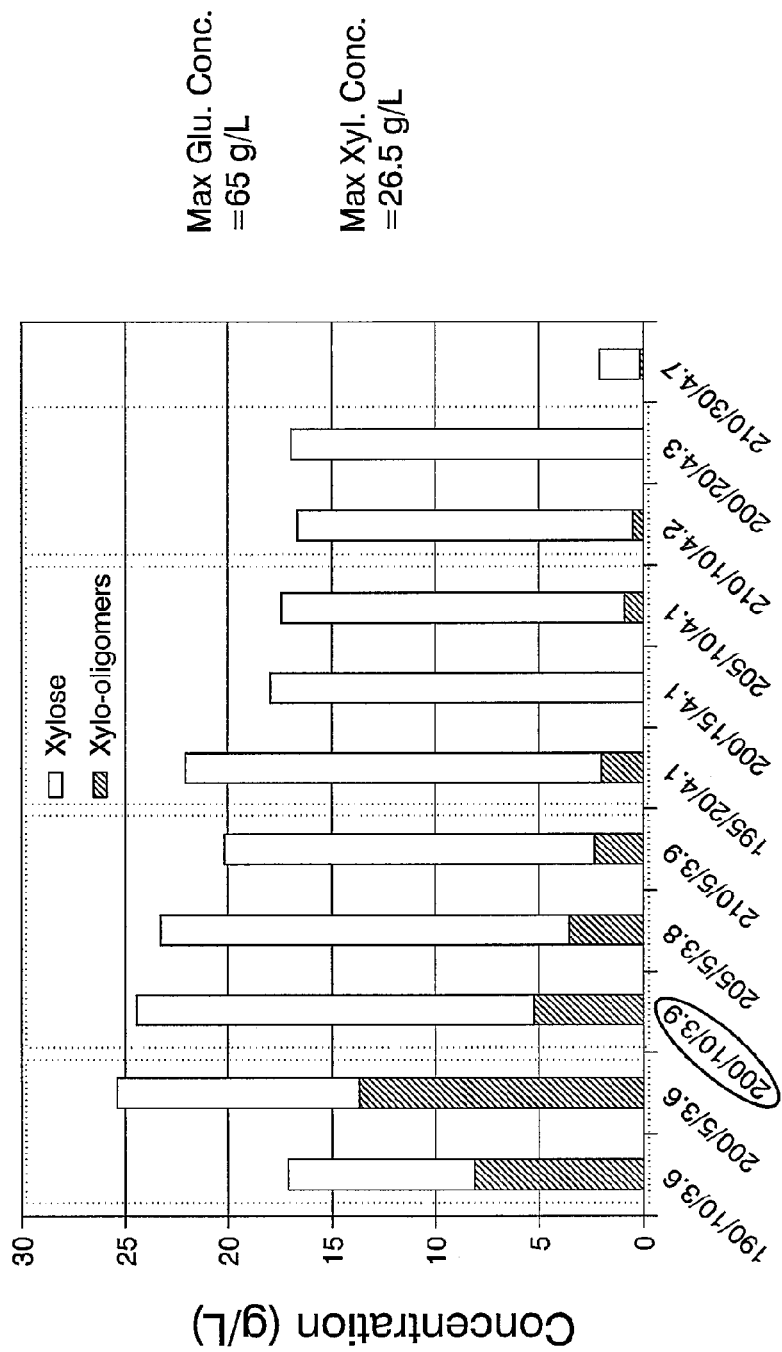
FIG. 4 provides a graph of xylose and xylo-oligomer concentration from treatment of 15% dry solids of mixed hardwood with 1% maleic acid under varied temperature/time conditions, as described further in Example 3.
Figure 5:
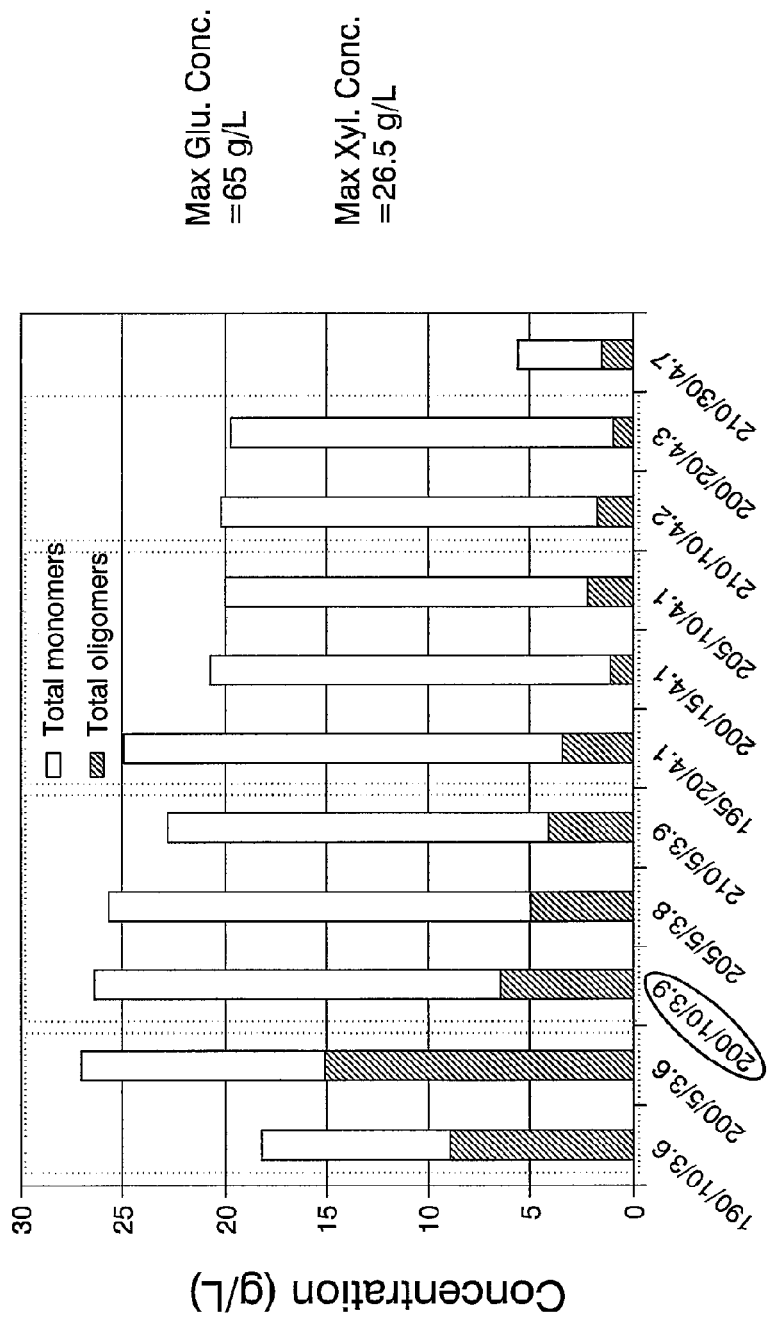
FIG. 5 provides a graph of total glucose and xylose monomer concentration and total gluco-oligomer and xylo-oligomer concentration from treatment of 15% dry solids of mixed hardwood with 1% maleic acid under varied temperature/time conditions, as described further in Example 3.
Figure 6:
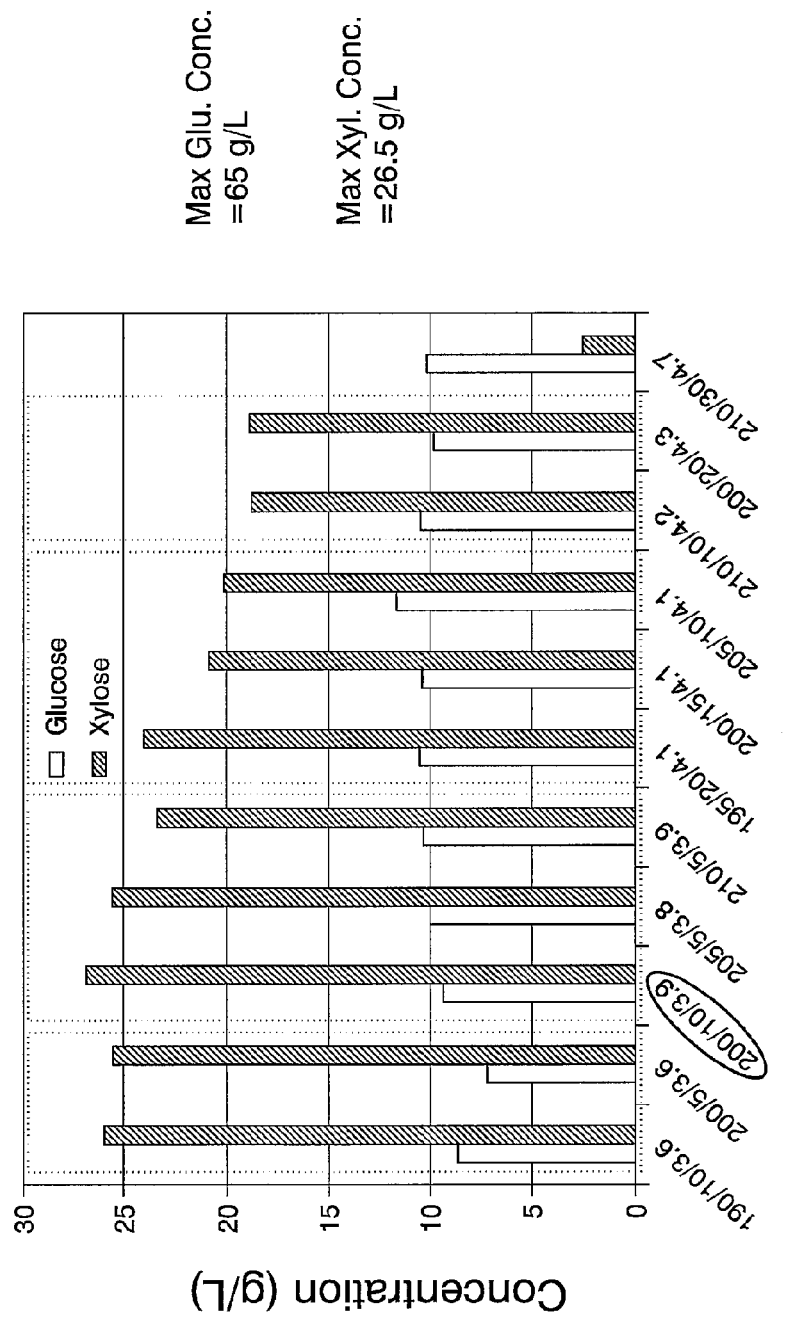
FIG. 6 provides a graph of glucose and xylose concentrations from a dual-step digestion including treatment of 15% dry solids of mixed hardwood with 1% maleic acid under varied temperature/time conditions followed by neutralization and a 24-hour cellulase digestion with 1 mg protein per gram of total dry solids biomass charged to the process, as described further in Example 4.
Figure 7:
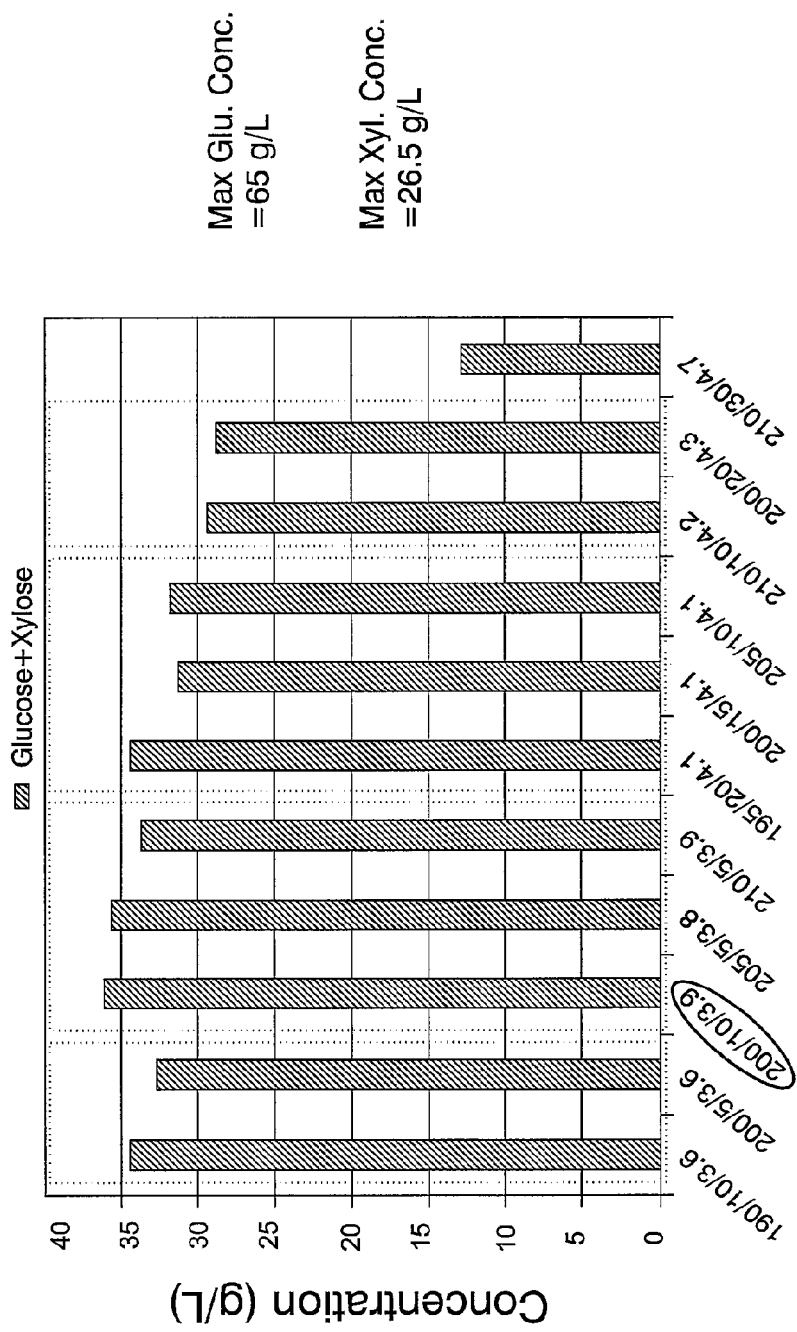
FIG. 7 provides a graph of total monomeric glucose and xylose concentration from the dual-step digestions plotted in FIG. 6 and described in Example 4.
Figure 8:
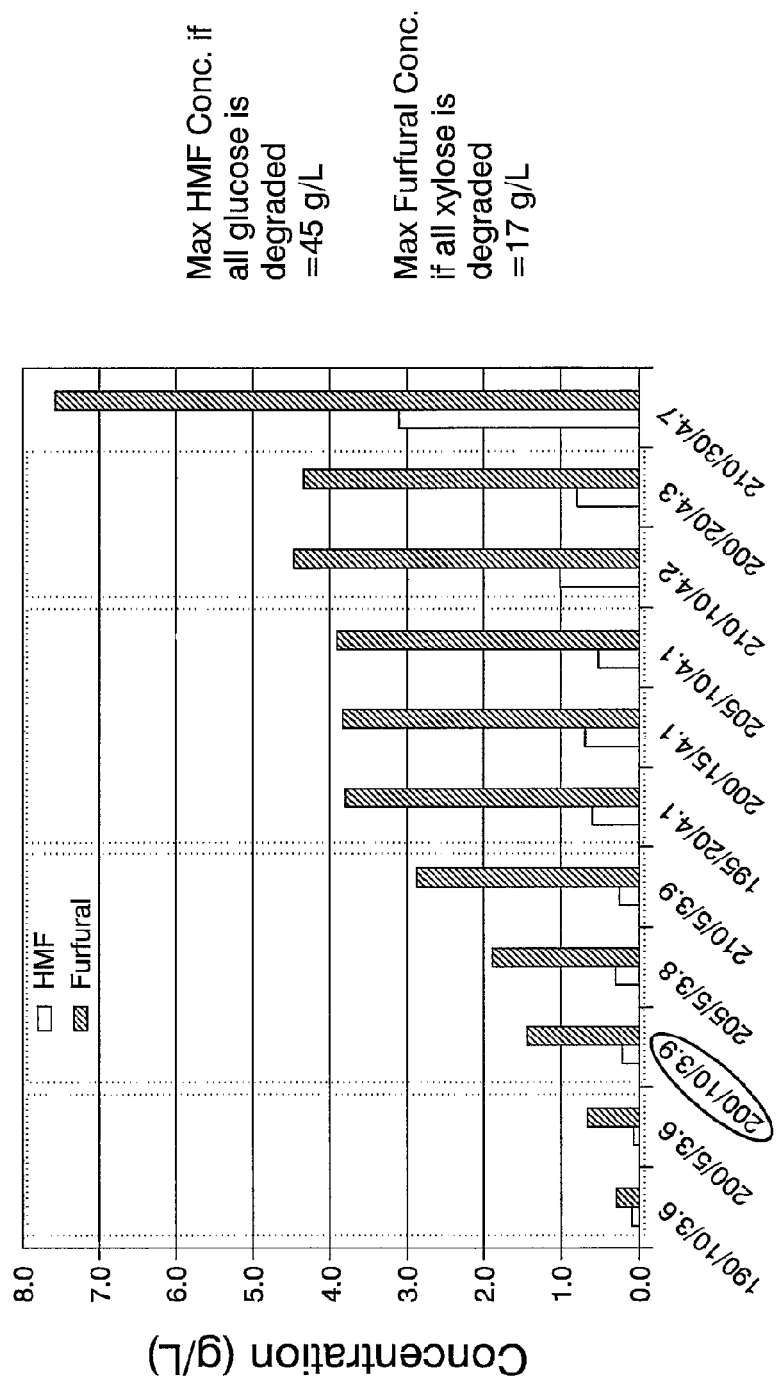
FIG. 8 provides a graph of 5-hydroxymethyl-furfural (HMF) and furfural concentrations for the dual-step digestions plotted in FIG. 6 and described in Example 4.

The liquefied fractions of the treated samples were assayed for concentrations of sugar monomers (glucose and xylose) and soluble oligomers, and for 5-hydroxymethylfurfural (HMF) and furfural as degradation products of the sugars. The results for varied times and temperatures for the runs, corresponding to varied Severity of treatment, are shown in FIGS. 3-8. As used for these Figures and elsewhere herein in reference to a biomass treatment: "Severity Factor"=log $(R_o)$= log $\{t \cdot \exp[(T-100)/14.75]\}$, where t is residence time in minutes, exp is exponent, and T is the target reaction temperature in ° C. FIGS. 3 and 4 show the concentrations of glucose and its oligomers and xylose and its oligomers, respectively, for the runs. As shown, the higher temperature runs gave generally higher conversion to glucose and xylose monomers, with the monomer levels decreasing in some of the highest temperature, longer runs, due to degradation of glucose to HMF and xylose to furfural. This degradation is also exhibited in FIG. 8 which charts correspondingly increase levels of furfural and HMF for the more severe runs. Total monomers and oligomers formed are shown in FIG. 5, and total glucose and xylose formed are shown in FIG. 6. From these and the other results it was demonstrated that highly advantageous liquefaction of the biomass occurred within the temperature/time conditions tested, particularly in those runs where the temperature was held at about 195-200° C. for periods of about 5-15 minutes.

Example 5

Enzyme Hydrolysis of Mimetic-Digested Biomass

Figure 9:
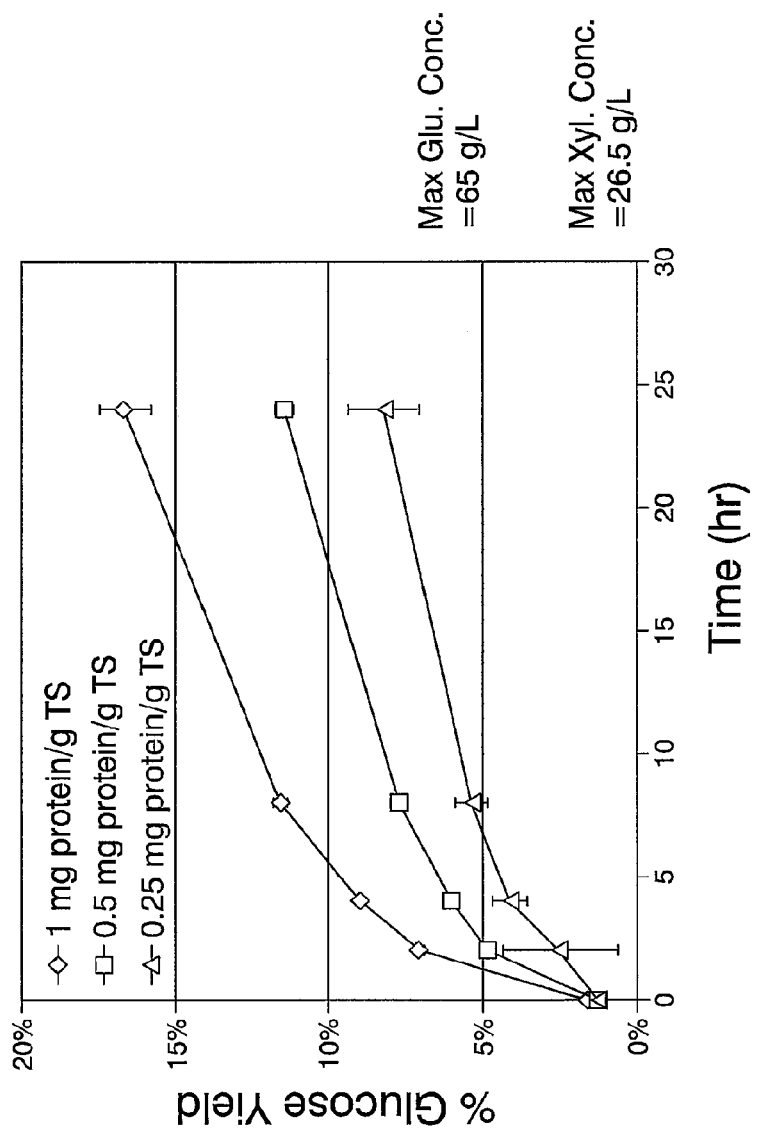
FIG. 9 provides a graph of monomeric glucose yields from dual-step digestions including treatment of 15% dry solids of mixed hardwood with 1% maleic acid under varied temperature/time conditions followed by neutralization and 24-hour cellulase digestions with 1, 0.5 and 0.25 mg protein per gram of total dry solids of biomass charged to the process, as described further in Example 5.
Figure 10:
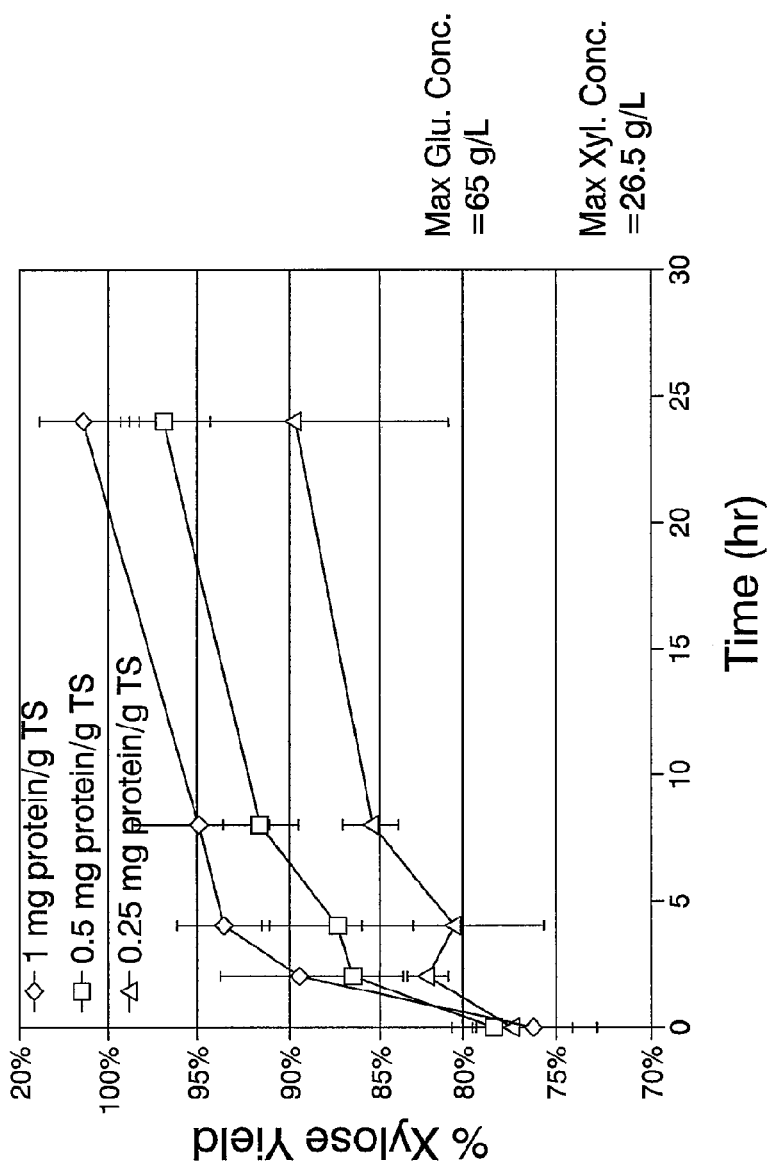
FIG. 10 provides a graph of monomeric xylose yields from the dual-step digestions plotted in FIG. 9 and described in Example 5.

This example demonstrates the enzymatic hydrolysis, at varied doses, of an overall biomass digest composition prior treated with a dicarboxylic acid (maleic acid). Mixed hardwood pin chip samples were digested as in Example 4 using the 5-minute heat-up, 10-minute treatment at 200° C. (1% Maleic Acid). The resulting digests as a whole were neutralized with ammonium hydroxide and charged respectively to a 250 mL Nalgene plastic bottle with varying doses of cellulase enzyme (Spezyme CP (Genencor, A Danisco Division); Novozyme 188 (Novozyme); Multifect Pectinase (Genencor, A Danisco Division)); 0.25 mg, 0.5 mg, or 1 mg enzyme per gram of total biomass solids, corresponding to about 0.375 FPU, 0.75 FPU and 1.5 FPU per gram of glucan in the raw biomass starting material). Enzyme hydrolysis was conducted for 24 hours at 50° C., pH 4.8, with stirring at 200 rpm, with samples taken at various intervals to measure glucose concentration. The results are shown in FIGS. 9 and 10. As shown in FIG. 9, the yield of glucose monomer (from enzymatic hydrolysis of glucan) after a 24 hour incubation period increased with increasing enzyme loading over the ranges tested, with all runs exceeding about 7% yield of glucose monomer after the 24 hour incubation, and total yields in excess of 10% being readily attainable during this period. Similarly, as shown in FIG. 10, the additional yield of monomeric xylose after the 24 hour incubation period increased with increasing enzyme loading, and in all runs exceeded 85% total yield after the combined mimetic and enzyme treatments, with total yields of about 90% to 100% being readily attainable after the 24 hour enzyme treatment. For purposes of these yield calculations, the total xylose and glucose available in the starting biomass feedstock was taken as 19 g xylose/100 g initial solids and 42 g glucose/100 g initial solids, respectively.

Example 6

Rheologic Properties of Liquefied Biomass

This example demonstrates that a digest composition of mixed hardwood resultant of sequential dicarboxylic acid (maleic acid) and enzyme hydrolysis exhibits advantageous rheologic properties for downstream unit operations. Samples of steam-exploded, mixed hardwood were subjected to sequential maleic acid and enzyme hydrolysis as described in Example 5, except using 20% by weight biomass solids instead of 15%, and using varied enzyme digestion periods of 2, 4, 8 and 24 hours. The entire resulting biomass digest composition was tested for rheologic properties with a Rheometer ARG2 (TA Instruments, Inc.) as follows.

Figure 11:
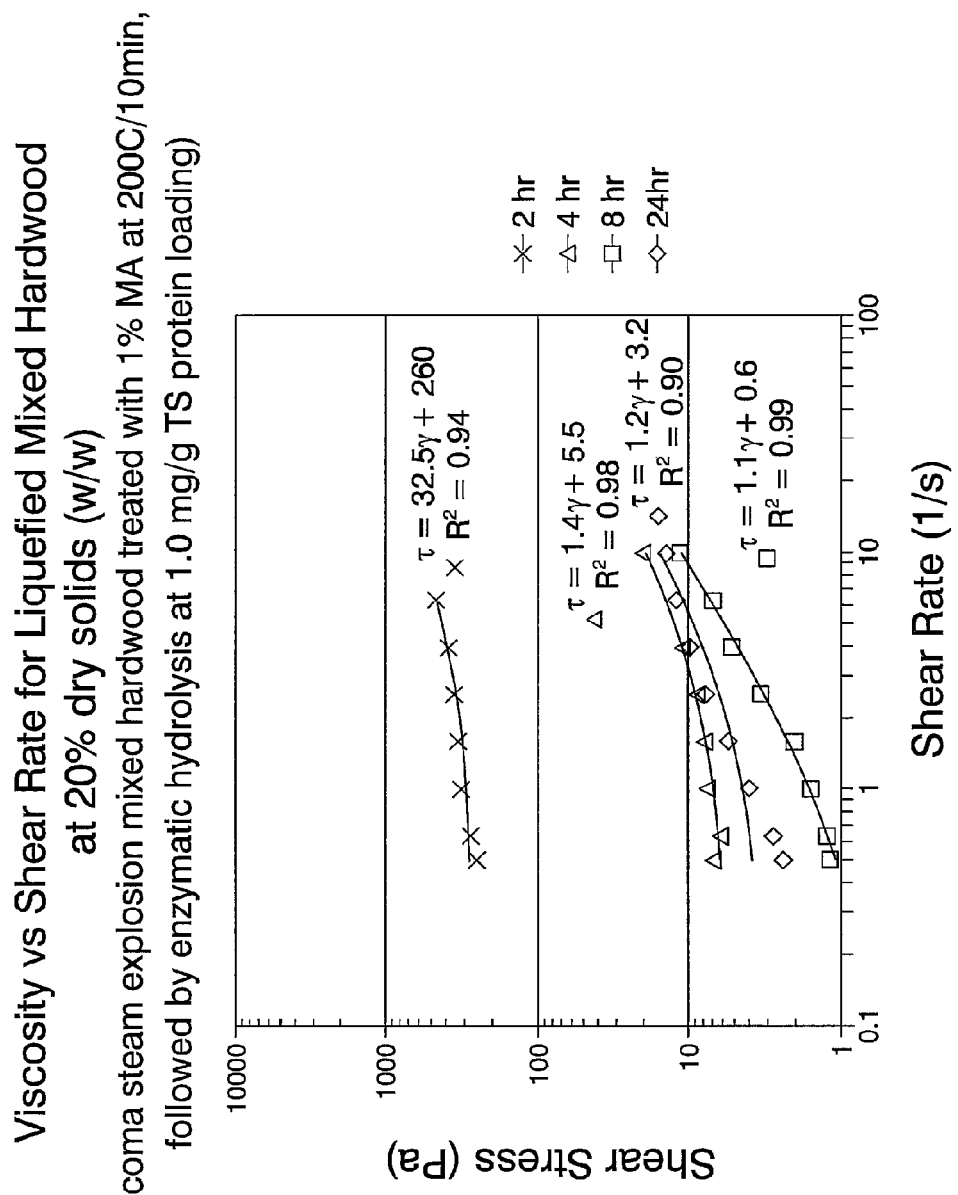
FIG. 11 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 1 mg protein per gram of total dry solids biomass charged to the process, as described further in Example 6.
Figure 12:
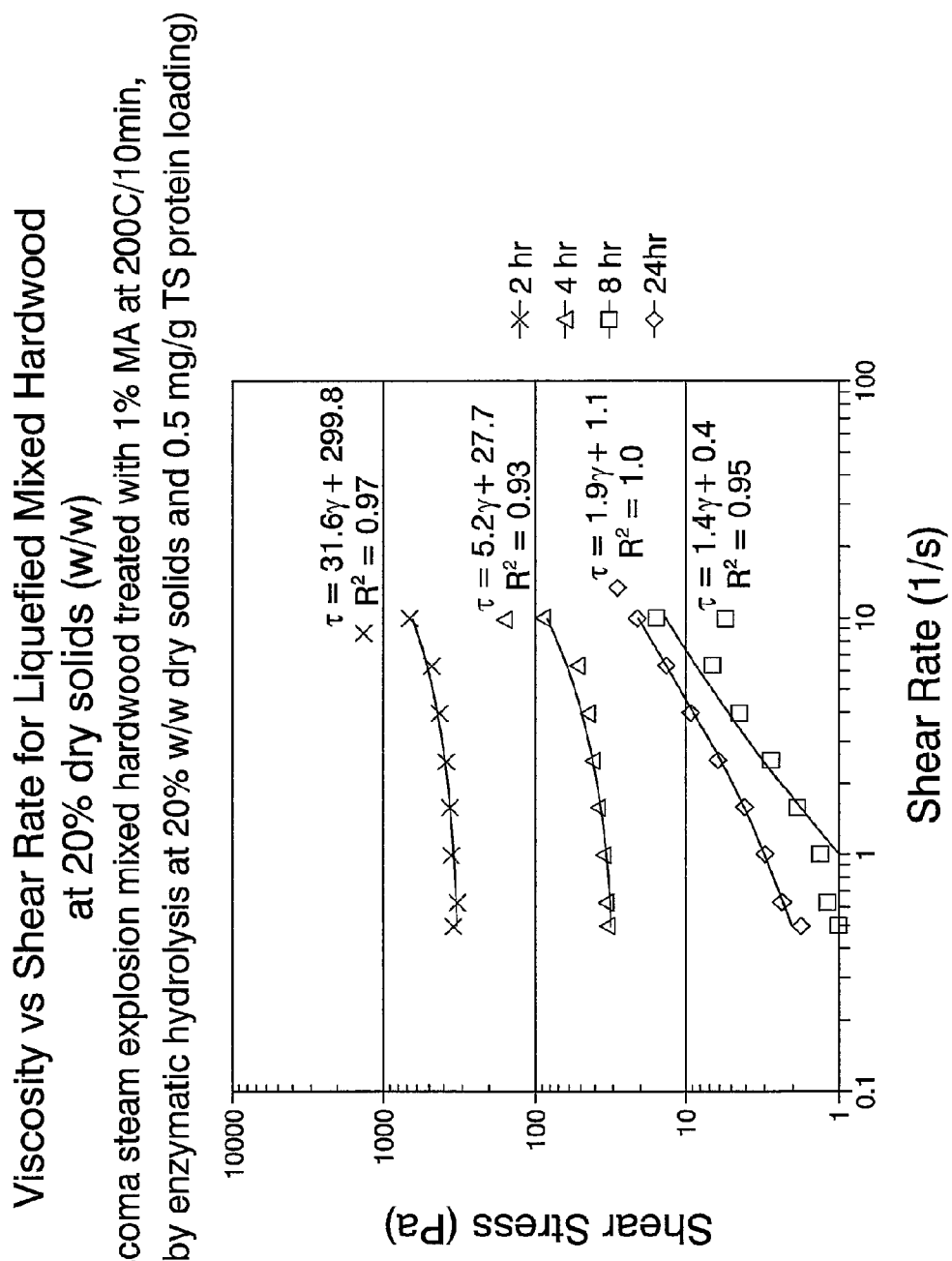
FIG. 12 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 0.5 mg protein per gram of total dry solids biomass charged to the process, as described further in Example 6.
Figure 13:
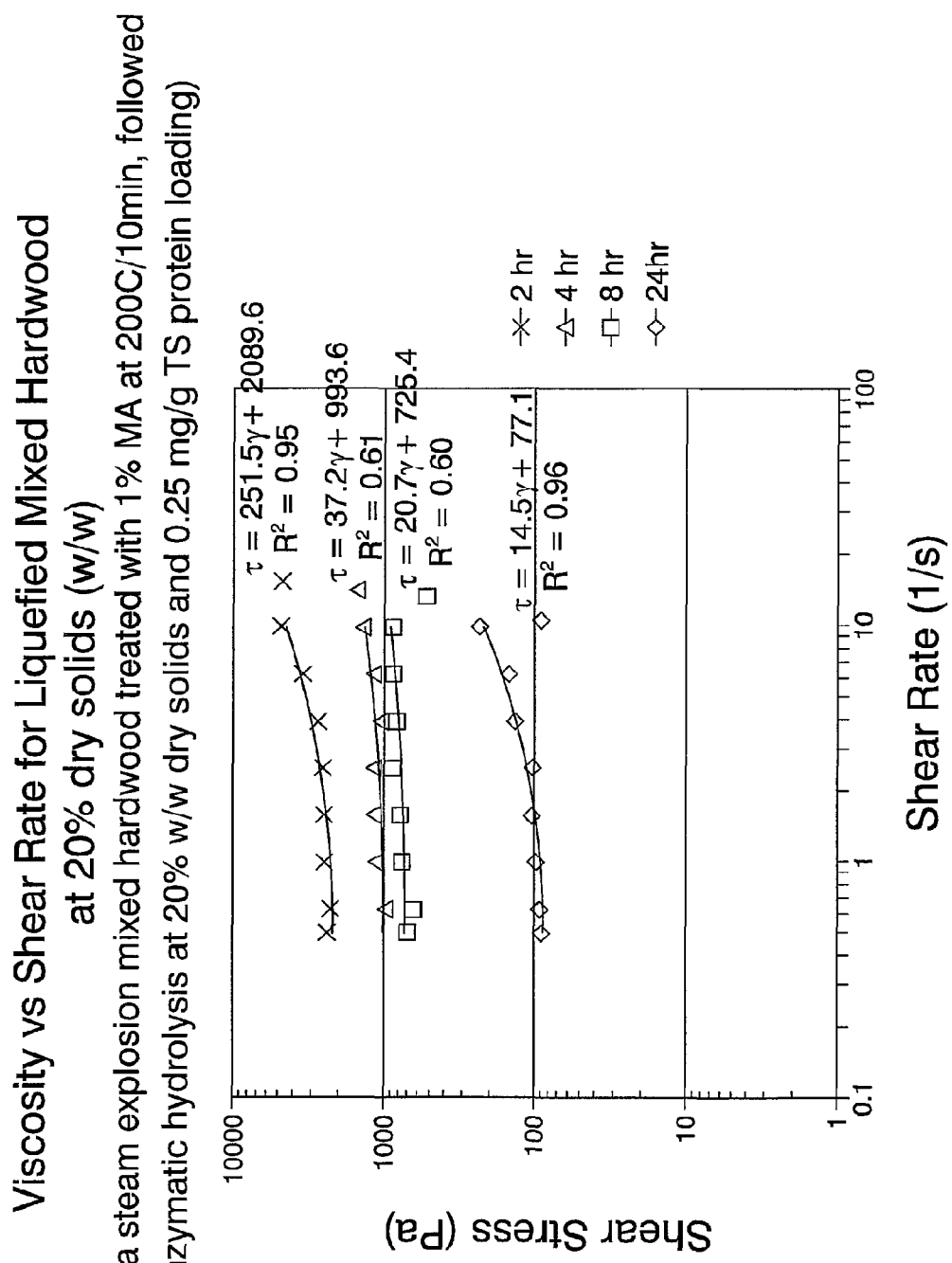
FIG. 13 provides a graph of shear stress (Pa) versus shear rate (1/s) for a liquefied composition from a dual-step digestion including treatment of 20% dry solids of previously steam-exploded, mixed hardwood with 1% maleic acid at 200° C. followed by neutralization and cellulase digestion for 2, 4, 8 or 24 hours with 0.25 mg protein per gram of total dry solids biomass charged to the process, as described further in Example 6.
Figure 14:
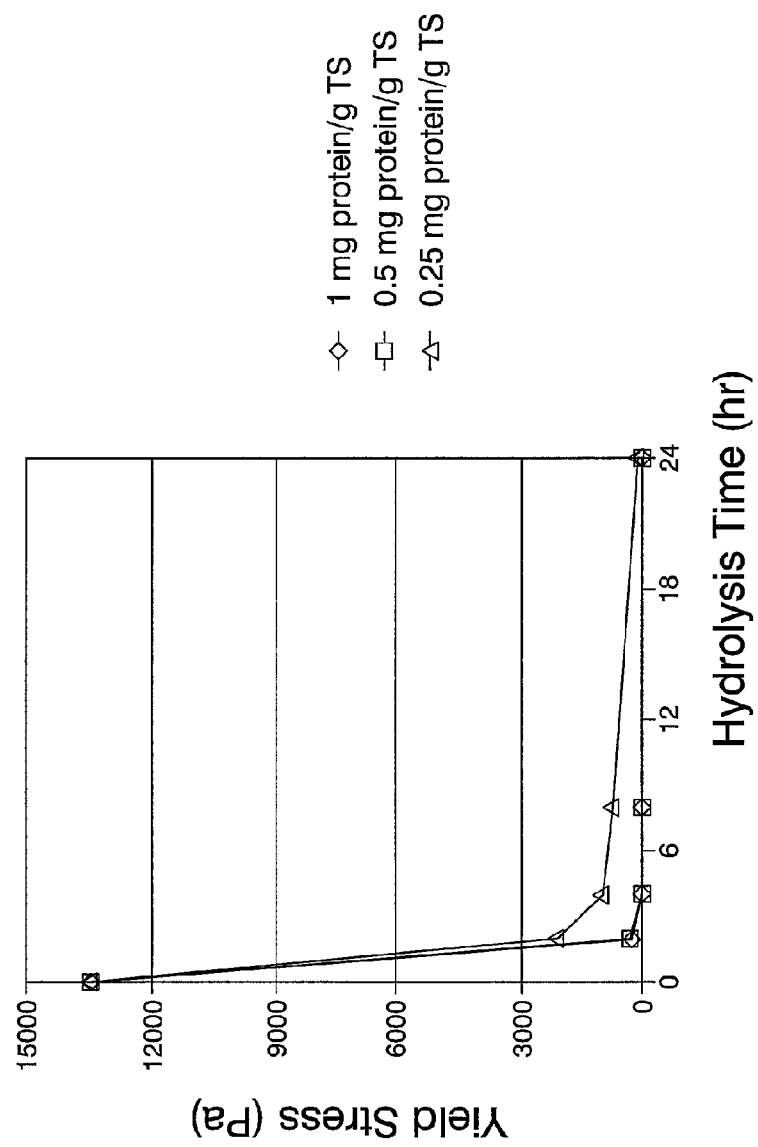
FIG. 14 provides a graph of yield stress (Pa) versus enzyme hydrolysis time for liquefied compositions from dual-step digestions including treatment of 20% dry solids of previously steam-exploded, mixed hardwood with 1% maleic acid at 200° C. followed by neutralization and cellulase digestion for 2, 4, 8 or 24 hours with 1, 0.5, and 0.25 mg protein per gram of total dry solids biomass charged to the process, as described further in Example 6.
Figure 15:
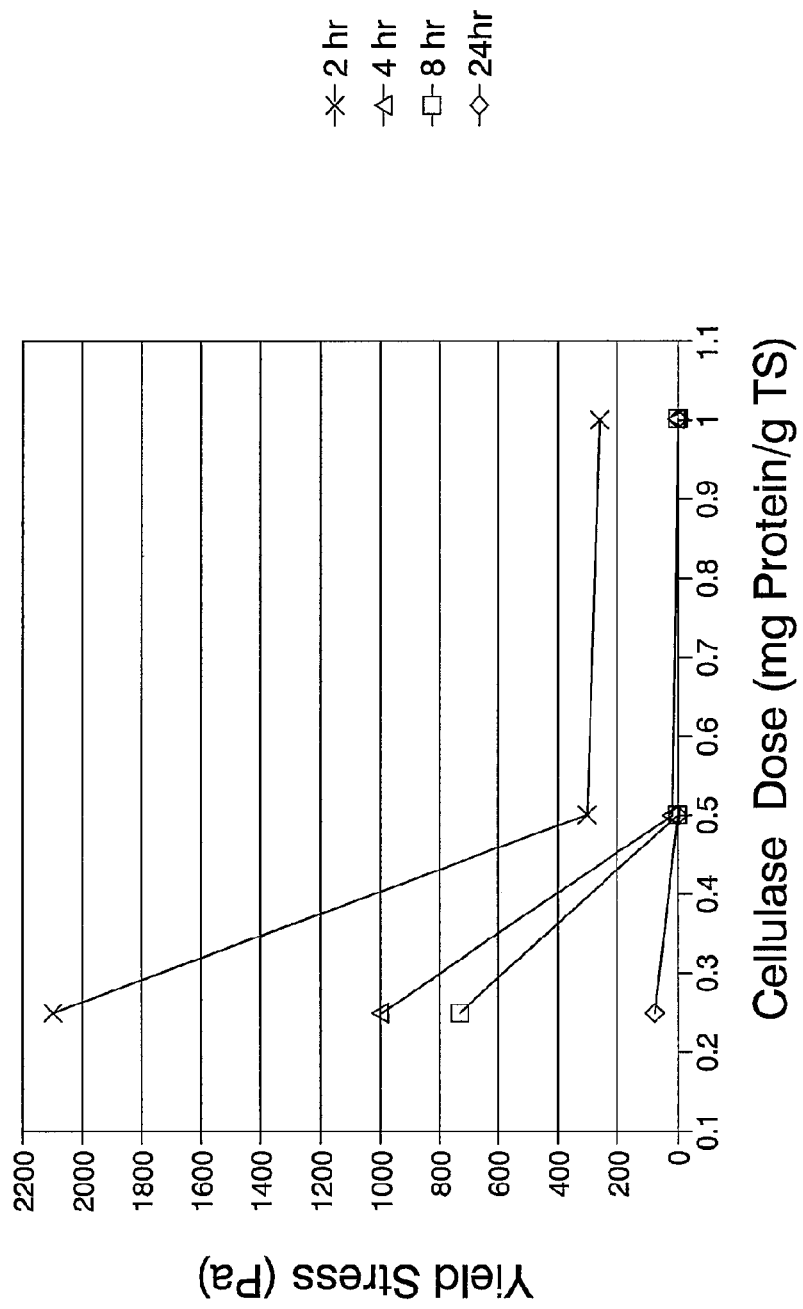
FIG. 15 provides a graph of yield stress (Pa) versus cellulase dose for liquefied compositions from the dual-step digestions also plotted in FIG. 14 and described in Example 6.

For the viscosity measurement, a steady state flow step was selected from the instrument setting. Approximately 5-10 mL of the sample was placed between two parallel plates with 1000 micrometer gap between the plates. A 20 mm diameter plate was used as the upper plate. All measurements were conducted at 25° C. Shear rate (1/s) was varied from 0.5 to 10. Yield stresses have been determined by extrapolating shear rate versus shear stress using the Bingham model (Barnes, J. Non-Newtonian Fluid Mech. Vol. 81, 133-178 (1999)): $\tau = \eta_p \gamma + \tau_y$; where $i$=shear stress (Pa); $\gamma$=shear rate (1/s); $\tau_y$=Bingham yield stress (Pa); and $\eta_p$=plastic viscosity (Pa·s). The results are presented graphically in FIGS. 11-15, which demonstrate that enzyme loadings and incubation times can be selected to significantly improve the flow properties of the biomass digest. FIGS. 11-13 plot shear stress (PA) versus shear rate (1/S) for the processed samples, and demonstrate that at enzyme loadings of 1 mg and 0.5 mg of protein per gram of biomass solids (FIGS. 11 and 12, respectively), the ratio of shear stress to shear rate remained relatively high for 2-hour enzyme incubation runs, whereas 4-hour, 8-hour and 24-hour enzyme incubation runs resulted in a comparatively much lower ratio of shear stress to shear rate. As shown in FIG. 13, significant improvements in flow properties of the biomass digest can be achieved even when using a very low enzyme loading of 0.25 mg protein per gram of total biomass solids, with longer incubation times providing a decreasing ratio of shear stress to shear rate in the studies. FIG. 14 plots the yield stress of the digest samples versus hydrolysis time for varied enzyme loadings, and FIG. 15 plots the yield stress of digest samples versus enzyme loading for various hydrolysis times. As shown, the yield stress of the digested biomass materials was very substantially decreased at all enzyme loadings, even after a relatively short (2 hour) enzyme incubation period. Generally, longer incubation periods and/or enzyme loadings can be selected to result in lower yield stress digest materials.

Example 7

Rheologic Properties of Liquefied Biomass

Figure 16:
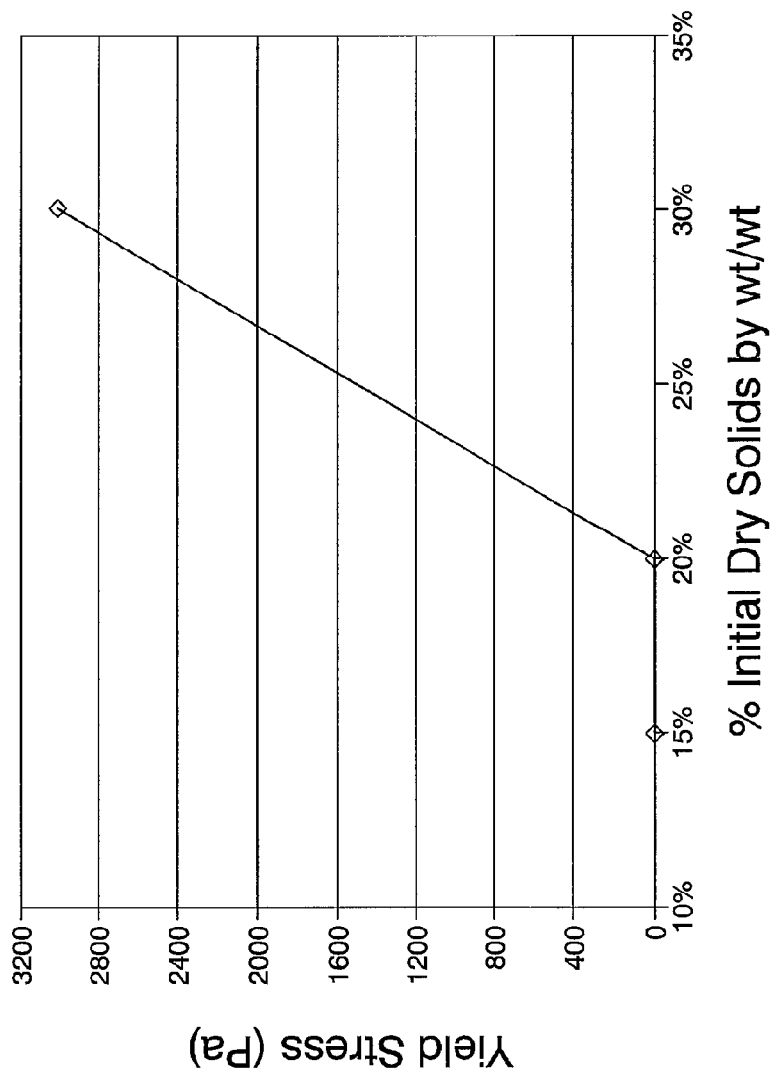
FIG. 16 provides a graph of yield stress (Pa) versus percent initial dry solids (wt/wt) for liquefied compositions from dual-step digestions including treatment of 15%, 20% and 30% dry solids of previously steam-exploded, mixed hardwood with 1% maleic acid at 200° C. followed by neutralization and cellulase digestion for 8 hours with 1 mg protein per gram of total dry solids biomass charged to the process, as described further in Example 7.
Figure 17:
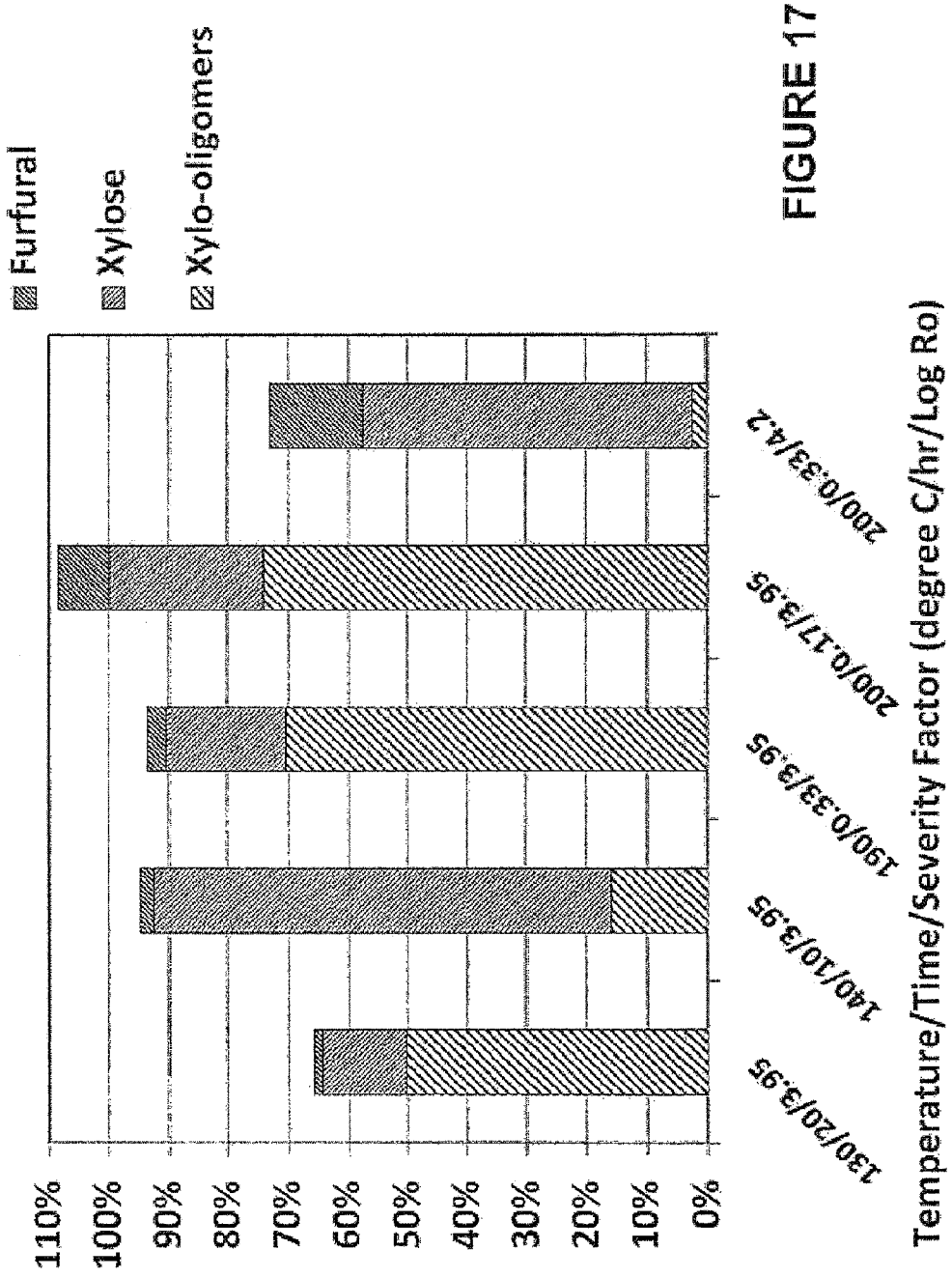
FIG. 17 provides a graph of xylose, xylo-oligomer and furfural concentration in digest slurries prepared as in Example 8.

This example demonstrates that digest compositions of mixed hardwood resultant of sequential dicarboxylic acid (maleic acid) and enzyme hydrolysis exhibit advantageous rheologic properties for downstream unit operations over varied dry solids loadings at the start of the process. Samples of steam-exploded, mixed hardwood were subjected to sequential maleic acid and enzyme hydrolysis as described in Example 5, except using 15%, 20% and 30% by weight biomass solids, and using an enzyme digestion period of 8 hours. The entire resulting biomass digest composition was tested for rheologic properties with a Rheometer ARG2 (TA Instruments, Inc.) and yield stresses for the samples were calculated as in Example 6. The results, shown in FIG. 16, demonstrate that under the conditions employed, increasing starting biomass solids loadings above 20% led to increasing yield stress values for the digest compositions. It will be understood that higher dicarboxylic acid (maleic acid) concentrations and/or longer incubation periods, for example, could be used to result in lower yield stress values for high-solids starting materials.

Example 8

Low-Temperature Mimetic Liquefaction

This example demonstrates that beneficial digest compositions of mixed hardwood can be prepared using low-temperature dicarboxylic acid (maleic acid) hydrolysis in which very highly-selective, enzyme-like activity is exhibited. Samples of steam-exploded, mixed hardwood were subjected to maleic acid hydrolysis at varied relatively low temperatures as follows.

Figure 18:
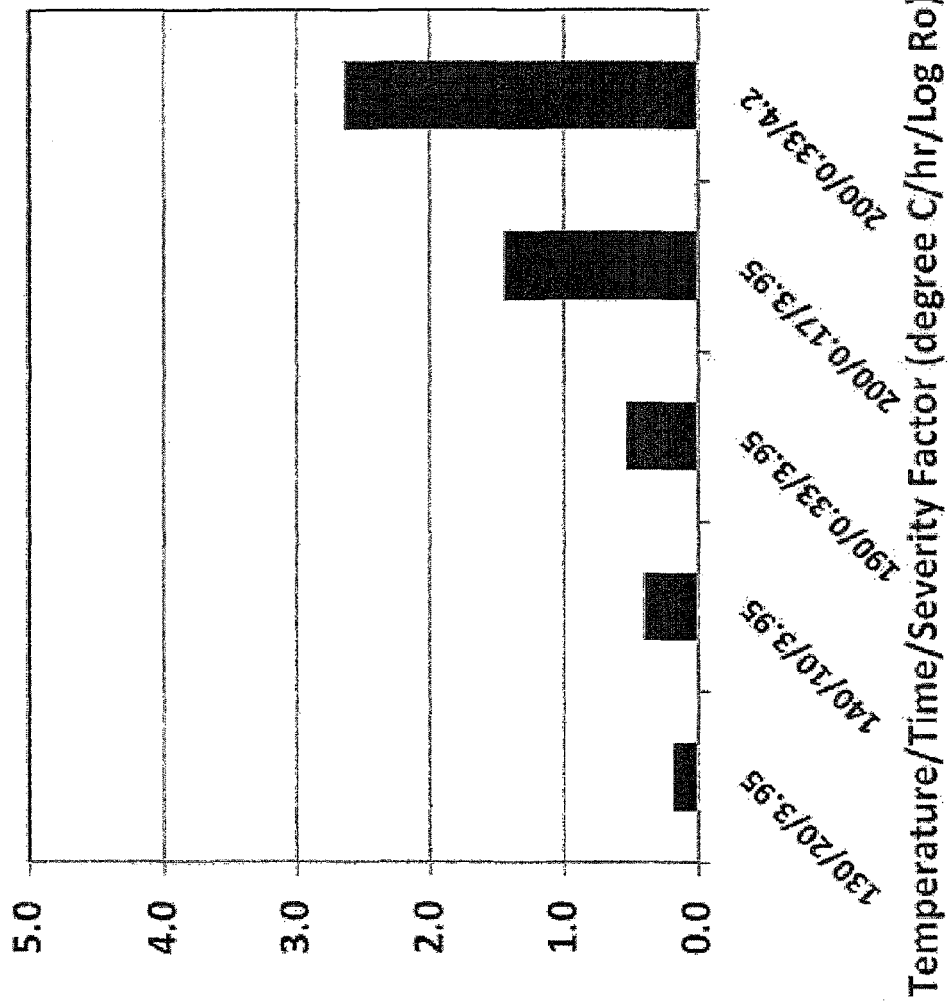
FIG. 18 provides a graph of furfural concentrations plotted in FIG. 17 and described in Example 8.
Figure 19:
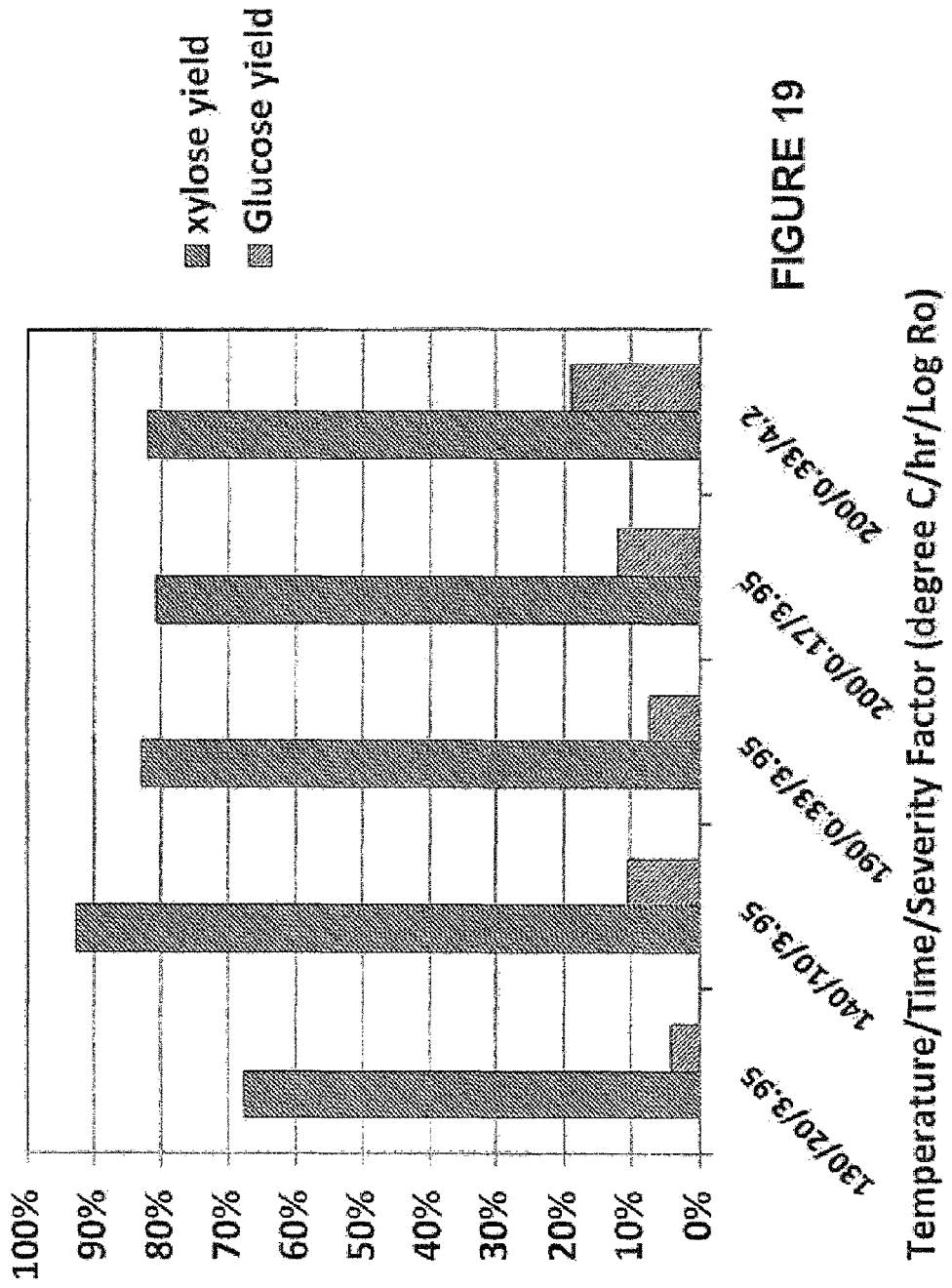
FIG. 19 provides a graph of monomeric glucose and xylose yields from dual-step digestions including treatment of 15% dry solids of mixed hardwood with 0.5% maleic acid under varied temperature/time conditions followed by neutralization and 24-hour cellulase digestions with 1 mg protein per gram of total dry solids of biomass charged to the process, as described further in Example 8.
Figure 20:
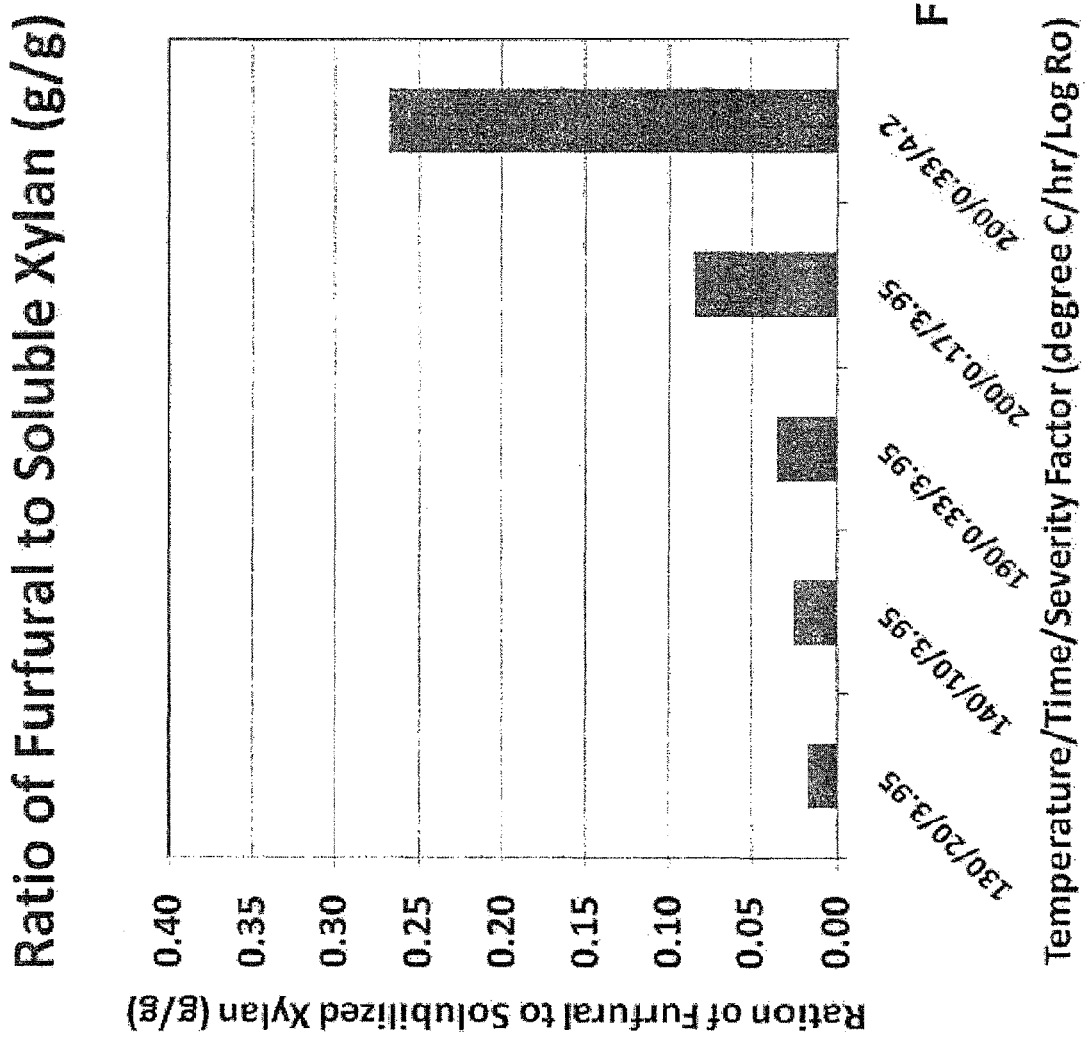
FIG. 20 provides a graph of the ratio of furfural to solubilized xylan in digest slurries from treatment of 15% dry solids of mixed hardwood with 0.5% maleic acid under varied temperature/time conditions, as described further in Example 8.

Samples (50-100 g each) of the mixed hardwood pin chips (average particle length about 0.5-1.0 inch) were soaked in the maleic acid solution overnight at solids loadings of 15%. The next day, in a sealed reaction vessel, the slurry was preheated to 140° C. for 10 minutes (essentially no reaction occurring) and then moved to a sandbath heated to the target temperature (Table 2). The samples were then given a period of 5 minutes to reach the target temperature and then kept in the sandbath for an additional period as shown in Table 2. The resulting digests as a whole were neutralized with ammonium hydroxide and charged respectively to a 250 mL Nalgene plastic bottle with cellulase enzyme (Spezyme CP (Genencor, A Danisco Division); Novozyme 188 (Novozyme); Multifect Pectinase (Genencor, A Danisco Division)) at 1 mg enzyme per gram of total starting biomass solids (dry weight). Enzyme hydrolysis was conducted for 24 hours at 50° C., pH 4.8, with stirring at 200 rpm, with samples taken at various intervals to measure glucose, gluco-oligomer, xylose, xylo-oligomer and furfural concentrations. The results are shown in FIGS. 17-20 and demonstrated significant liquefaction and saccharification of the biomass by the dicarboxylic acid mimetic with high selectivity for fermentable sugar. The selectivity for soluble xylose and xylo-oligomers ("soluble xylan") versus furfural in the mimetic-pretreated digest was surprisingly good at longer times and lower temperatures while also providing good sugar yields (see FIGS. 17 and 20). Correspondingly, the furfural concentration in the mimetic-pretreated digest was higher in the samples treated at higher temperatures and for shorter times (FIG. 18). The xylose and glucose yields after mimetic pretreatment and subsequent enzymatic hydrolysis (PT-EH) are shown in FIG. 19, with good yields being obtainable even in relatively low temperature runs.

TABLE 2

Severity defined as a function of times and temperatures

| Temperature (° C.) | Time (hr) | severity factor (Log $R_o$) |
|---|---|---|
| 130 | 20 | 3.95 |
| 140 | 10 | 3.95 |
| 190 | 0.33 | 3.95 |
| 200 | 0.17 | 3.95 |
| 200 | 0.33 | 4.2 |

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

The invention claimed is:

1. A method for liquefaction of solid lignocellulosic biomass, comprising:
    (a) contacting the solid lignocellulosic biomass with a dicarboxylic acid for a period of time and under conditions effective to form an acidic mixture containing liquefied lignocellulosic biomass components and unliquefied lignocellulosic biomass components, wherein said contacting is conducted in the presence of from about 0.1% to 2% of the dicarboxylic acid relative to the lignocellulosic biomass on a dry weight basis, wherein said contacting is conducted with said dicarboxylic acid in an aqueous medium, and wherein the aqueous medium is at least 80% by weight aqueous;
    (b) neutralizing the acidic mixture to form a neutralized mixture containing the liquefied lignocellulosic biomass components and unliquefied lignocellulosic biomass components, wherein said liquefied lignocellulosic biomass components in the neutralized mixture comprise phenols; and
    (c) after said neutralizing, enzymatically hydrolyzing the unliquefied lignocellulosic biomass components in the presence of at least a portion of the liquefied lignocellulosic biomass components, wherein said enzymatically hydrolyzing is conducted sufficiently to form a flowable enzyme-hydrolyzed composition fluid having a yield stress of less than about 1000 Pascals, and wherein said enzymatically hydrolyzing is conducted in the presence of a cellulase enzyme at a level of 3 Filter Paper Units or less per gram of glucan in the solid lignocellulosic biomass.

2. The method of claim 1, wherein the dicarboxylic acid is selected from maleic acid, succinic acid, and oxalic acid.

3. The method of claim 2, wherein the dicarboxylic acid is maleic acid.

4. The method of claim 1, wherein the lignocellulosic biomass is wood.

5. The method of claim 1, wherein said contacting the lignocellulosic biomass is at a temperature of at least about 100° C.

6. The method of claim 1, wherein said contacting the lignocellulosic biomass is for a period of up to about 60 minutes.

7. The method of claim 1, wherein said enzymatically hydrolyzing is performed with the cellulase enzyme at a concentration of less than about 2 milligrams per gram of the lignocellulosic biomass dry matter.

8. The method of claim 1, wherein said liquefied lignocellulosic biomass components in the neutralized mixture comprise furfural and 5-hydroxymethylfurfural.

9. A method for liquefaction of wood biomass, comprising:
    (a) forming a mixture including an aqueous solution of a dicarboxylic acid and solid, particulate wood biomass containing hemicellulose, wherein said aqueous solution of a dicarboxylic acid is at least 80% by weight aqueous, wherein said mixture contains about 0.1 to 2% of the dicarboxylic acid relative to the wood biomass on a dry weight basis, and wherein the solid, particulate wood biomass comprises elongate fibrous particles having an average length of at least 1 mm; and
    (b) incubating the mixture for a period of time and under conditions effective to cause hydrolysis of the wood biomass substantially by the dicarboxylic acid to form a flowable composition and to achieve greater than 70% hydrolysis of the hemicellulose to xylose; and further wherein the formed flowable composition has a total monomeric xylose content of at least 15 g/L and a total furfural content of less than 5 g/L.

10. The method of claim 9, wherein the elongate fibrous particles have an average length of about 2 to 4 cm.

11. The method of claim 9, wherein the dicarboxylic acid is selected from maleic acid, succinic acid, and oxalic acid.

12. The method of claim 11, wherein the dicarboxylic acid is maleic acid.

13. The method of claim 9, wherein said forming is conducted so as to achieve an initial loading of the wood biomass in the mixture of at least 15% by weight based on the dry weight of the wood biomass.

14. The method of claim 9, wherein said incubating is conducted sufficiently to liquefy at least 10% by weight of the wood biomass dry matter.

15. The method of claim 9, further comprising the step of neutralizing the flowable composition to form a neutralized composition.

16. The method of claim 9, wherein the dicarboxylic acid constitutes greater than 50%, on a molar basis, of the organic protic species in the aqueous solution.

17. The method of claim 9, wherein the aqueous solution is essentially free of organic protic species other than the dicarboxylic acid.

18. A method for liquefaction of lignocellulosic wood biomass, comprising:
   (a) forming a mixture including an aqueous solution of a dicarboxylic acid and solid, particulate lignocellulosic wood biomass containing hemicellulose, with the biomass present at a level of at least 10% by weight in the mixture, wherein said mixture contains about 0.1 to 2% of the dicarboxylic acid relative to the lignocellulosic wood biomass on a dry weight basis, wherein said aqueous solution of a dicarboxylic acid is at least 80% by weight aqueous, and wherein the particulate lignocellulosic wood biomass has an average maximum particle dimension of at least 3 mm; and
   (b) incubating the mixture at a temperature and for a period of time (i) sufficient to form a flowable biomass composition in which at least about 20% of the biomass solids have been converted to biomass components dissolved in the solution, (ii) sufficient to achieve greater than 70% hydrolysis of the hemicellulose to xylose, and (iii) sufficient to form the flowable biomass composition having a total monomeric xylose content of at least 15 g/L and a total furfural content of less than 5 g/L.

19. The method of claim 18, wherein the incubating is effective to increase the bulk density of the solids by at least about 15%.

20. The method of claim 18, wherein said incubating occurs in a first vessel, and also comprising the step of pumping the flowable biomass composition through a conduit to a second vessel.

21. A method for treating lignocellulosic wood biomass, comprising:
   contacting a starting lignocellulosic wood biomass with a dicarboxylic acid for a period of time and under conditions effective to form an acidic mixture containing liquefied lignocellulosic biomass components and unliquefied lignocellulosic biomass components, wherein said contacting is conducted with said dicarboxylic acid in a liquid aqueous medium, and wherein the aqueous medium is at least 80% by weight aqueous;
   neutralizing the acidic mixture to form a mixture containing dicarboxylate anions, cations, liquefied lignocellulosic wood biomass components including xylose, glucose phenols, and unliquefied lignocellulosic wood biomass components; and
   contacting the mixture containing dicarboxylate anions, cations, liquefied lignocellulosic wood biomass components including xylose, glucose, phenols, and unliquefied lignocellulosic wood biomass components, with a cellulase enzyme at a level of 3 Filter Paper Units or less per gram of glucan in the starting lignocellulosic wood biomass for a period of time and under conditions effective to hydrolyze at least a portion of the unliquefied lignocellulosic biomass components, wherein said contacting is conducted sufficiently to form a flowable enzyme-hydrolyzed composition fluid having a yield stress of less than about 1000 Pascals.

22. The method of claim 21, wherein the dicarboxylate anions are maleate anions.

23. The method of claim 21, wherein the lignocellulosic biomass components are wood components.

24. The method of claim 21, wherein said contacting is conducted with the cellulase enzyme at a loading less than about 2 milligrams per gram of the lignocellulosic biomass on a dry weight basis.

25. The method of claim 21, further comprising isolating a solids-free liquid including the xylose and the glucose after said contacting.

26. The method of claim 21, further comprising:
   forming said mixture by incubating particulate lignocellulosic biomass in contact with a liquid medium comprising a dicarboxylic acid.

27. A method for manufacturing ethanol, comprising:
   (a) first contacting lignocellulosic biomass with a dicarboxylic acid for a period of time and under conditions effective to form an acidic mixture containing liquefied lignocellulosic biomass components including glucose, xylose, phenols, and unliquefied lignocellulosic biomass components, wherein said first contacting is conducted in the presence of from about 0.1% to 2% of the dicarboxylic acid relative to the lignocellulosic biomass on a dry weight basis, wherein said first contacting is conducted with said dicarboxylic acid in an aqueous medium, and wherein the aqueous medium is at least 80% by weight aqueous;
   (b) neutralizing the acidic mixture to form a neutralized mixture containing the liquefied lignocellulosic biomass components including glucose, xylose, phenols, and unliquefied lignocellulosic biomass components;
   (c) second contacting the neutralized mixture with a cellulase enzyme for a period of time and under conditions effective to liquefy at least a portion of the unliquefied lignocellulosic biomass and form an enzymatically-hydrolyzed mixture including glucose and xylose; and
   (d) fermenting a medium containing the glucose and xylose from the enzymatically-hydrolyzed mixture to form ethanol.

28. The method of claim 27, wherein the dicarboxylic acid is maleic acid.

29. The method of claim 27, wherein the lignocellulosic biomass comprises wood.

30. The method claim 27, wherein said second contacting and fermenting steps occur simultaneously in a single chamber.

31. The method of claim 1, wherein the aqueous medium is at least 90% by weight aqueous.

32. A method for treating lignocellulosic wood biomass, comprising:
   providing a mixture including lignocellulosic wood biomass and an aqueous medium containing a dicarboxylic acid, wherein the lignocellulosic wood biomass comprises elongate wood particles having an average length of at least 1 mm, wherein the aqueous medium is at least 80% by weight aqueous, and wherein the mixture is constituted at least 15% by weight of the lignocellulosic wood biomass based on the dry weight of the lignocellulosic wood biomass;
   incubating the mixture for a period of time and under conditions effective to cause hydrolysis of the wood biomass by the dicarboxylic acid to form a flowable composition.

33. The method of claim 32, wherein:
   said dicarboxylic acid is selected from maleic acid, oxalic acid and succinic acid;

said mixture contains about 0.1 to 2% of the dicarboxylic acid relative to the lignocellulosic wood biomass on a dry weight basis; and said incubating is effective to solubilize 20% to 60% of the lignocellulosic wood biomass, on a dry weight basis, in the aqueous medium.

\* \* \* \* \*